(12) United States Patent
Furuzono et al.

(10) Patent No.: US 8,360,000 B2
(45) Date of Patent: Jan. 29, 2013

(54) FLOCKED MEDICAL INSTRUMENT TO BE PLACED IN THE BODY, METHOD OF PRODUCING THE MEDICAL INSTRUMENT TO BE PLACED IN THE BODY AND APPARATUS FOR PRODUCING THE MEDICAL INSTRUMENT TO BE PLACED IN THE BODY

(75) Inventors: Tsutomu Furuzono, Mino (JP); Shoji Yasuda, Kunitachi (JP); Toshiyuki Imoto, Kyoto (JP)

(73) Assignee: Japan Science and Technology Agency, Saitama (JP)

( * ) Notice: Subject to any disclaimer, the term of this patent is extended or adjusted under 35 U.S.C. 154(b) by 952 days.

(21) Appl. No.: 12/095,120

(22) PCT Filed: Nov. 27, 2006

(86) PCT No.: PCT/JP2006/323621
§ 371 (c)(1),
(2), (4) Date: Apr. 6, 2009

(87) PCT Pub. No.: WO2007/061100
PCT Pub. Date: May 31, 2007

(65) Prior Publication Data
US 2009/0306599 A1  Dec. 10, 2009

(30) Foreign Application Priority Data

Nov. 28, 2005 (JP) .................................. 2005-342740

(51) Int. Cl.
*B05B 5/057* (2006.01)
(52) U.S. Cl. ........................................ 118/638; 118/621
(58) Field of Classification Search .................. 118/638, 118/621
See application file for complete search history.

(56) References Cited

U.S. PATENT DOCUMENTS 2,927,584 A * 3/1960 Wallace .................... 604/103.08
2,992,126 A * 7/1961 Kenneth et al. ................ 118/638
(Continued)

FOREIGN PATENT DOCUMENTS

| CA | 2475023 A1 | 12/2003 |
| EP | 0315305 A2 | 5/1989 |

(Continued)

OTHER PUBLICATIONS

"Facts of Flocking Process." (Aug. 1, 1979). New Polymer Publishing, N. Iinuma, Polymer Publishing Inc., published Aug. 1, 1979, vol. 17, pp. 1-11.
(Continued)

*Primary Examiner* — Dah-Wei Yuan
*Assistant Examiner* — Stephen Kitt
(74) *Attorney, Agent, or Firm* — Morrison & Foerster LLP

(57) ABSTRACT

The present invention provides a percutaneous terminal having a substrate thereof flocked with fibers having bio-affinity, and thereby being able to adhere tightly to a living body, a medical instrument to be placed in the body, and a production method and a production apparatus of the percutaneous terminal and the medical instrument to be placed in the body. The percutaneous terminal according to the present invention is one which the surface of the substrate is flocked with bio-affinitive short fibers (e.g. hydroxyapatite complex particles), therefore the bio-affinitive short fibers are risen perpendicular to or substantially perpendicular to the surface of the substrate. As a result, an area of the bio-affinitive short fibers coating a unit area of the substrate of the percutaneous terminal to the unit area of the percutaneous terminal substrate is considerably elevated and, in its turn, the adhesiveness of the percutaneous terminal to biological tissues is improved. Thus, it is possible to stably fix to the living body a medical device such as a catheter or the like which has the percutaneous terminal. The medical instrument according to the present invention is also flocked with the short fibers as described above, therefore it is possible to stably fix to the living body the medical instrument to be placed in the body.

6 Claims, 12 Drawing Sheets

U.S. PATENT DOCUMENTS

| | | | |
|---|---|---|---|
| 4,820,289 | A | 4/1989 | Coury et al. |
| 4,871,384 | A | 10/1989 | Kasuga |
| 5,747,133 | A | 5/1998 | Vinod et al. |
| 2004/0033334 | A1 | 2/2004 | Merovitz |
| 2005/0119732 | A1 | 6/2005 | Furuzono et al. |

FOREIGN PATENT DOCUMENTS

| | | |
|---|---|---|
| EP | 1508586 A1 | 2/2005 |
| JP | 01-107768 | 4/1989 |
| JP | 06-141926 | 5/1994 |
| JP | 06-327757 | 11/1994 |
| JP | 07-116557 | 5/1995 |
| JP | 07-303691 | 11/1995 |
| JP | 07-306201 | 11/1995 |
| JP | 08-056963 | 3/1996 |
| JP | 08-206193 | 8/1996 |
| JP | 10-015061 | 1/1998 |
| JP | 2000-342676 | 12/2000 |
| JP | 2001-172511 | 6/2001 |
| JP | 2003-038596 | 2/2003 |
| JP | 2005-112848 A | 4/2005 |
| JP | 2005-319002 A | 11/2005 |
| WO | WO-98/27265 A1 | 6/1998 |
| WO | WO-2007/007452 A1 | 1/2007 |

OTHER PUBLICATIONS

Aoki, H. (1994). "Percutaneous Devices," Chapter 6, in *Medical Applications of Hydroxyapatite*, Ishiyaky EuroAmerica, Inc.: Tokyo, St. Louis, pp. 133-155.

Furuzono, T. et al. (2004). "Nano-scaled Hyroxyapatite/Polymer Composite IV. Fabrication and Cell Adhesion Properties of a Three-dimensional Scaffold Made of Composite Material with a Silk Fibroin Substrate to Develop a Percutaneous Device," *The Japanese Society for Artificial Organs* 7:137-144.

Furuzono et al., "Synthesis and Function of Calcined Hydroxyapatite Coated Silicone", Fiber Preprints, Japan, vol. 56, No. 2, 2001, p. 59, (Total 5 pages, 3 pages of English Translation and 2 pages of Official Copy).

Szycher et al., "Advances in Textured Blood Interfaces", Society of Plastic Engineers, 38th Annual Technical Conference, vol. 38, May 1980, pp. 622-624.

Furuzono et al., "A Novel Composite Material for Catheter Showing Bio-adhesiveness and Antibacterial Effect", Materials Integration, vol. 18, No. 6, 2005, pp. 46-49, (Total 17 pages, 12 pages of English Translation and 5 pages of Official Copy).

Okada et al., "Conditions for Biomaterials and Medicals Devices", Clinical Engineering, vol. 16, No. 9, 2005, pp. 959-966, (Total 25 pages, 16 pages of English Translation and 9 pages of Official Copy).

Office Action received for Japanese Patent Application No. 2007-546527, mailed on Jun. 21, 2011, 7 pages (5 pages of English Translation and 2 pages of Official Copy).

International Search Report mailed Mar. 6, 2007, for PCT Application No. PCT/JP2006/323621 filed Nov. 27, 2006, 3 pages.

"Facts of Flocking Process," (Aug. 1, 1979). N. Iinuma, Polymer Publishing Inc., vol. 17, pp. 1-11. (Partial English translation attached, 1 page).

Aoki, H. (1994). "Percutaneous Devices" Chapter 6 In *Medical Applications of Hydroxyapatite*. Ishiyaku EuroAmerica, Inc.: Tokyo, St. Louis, pp. 133-155.

Furuzono, T. et al. (2004). "Nano-Scaled Hydroxyapatite/Polymer Composite IV. Fabrication and Cell Adhesion Properties of a Three-Dimensional Scaffold Made of Composite Material with a Silk Fibroin Substrate to Develop a Percutaneous Device," *Journal of Artificial Organs* 7:137-144.

Office Action received for Japanese Patent Application No. 2007-546527, mailed on Jan. 10, 2012, 7 pages (5 pages of English translation and 2 pages of Office Action).

Extended European Search Report received for European Patent Application No. 06833425.9, mailed on Jan. 26, 2011, 9 pages.

\* cited by examiner

INSERTING DIRECTION

INSERTING DIRECTION

FLOCKED MEDICAL INSTRUMENT TO BE PLACED IN THE BODY, METHOD OF PRODUCING THE MEDICAL INSTRUMENT TO BE PLACED IN THE BODY AND APPARATUS FOR PRODUCING THE MEDICAL INSTRUMENT TO BE PLACED IN THE BODY

CROSS REFERENCE TO RELATED APPLICATIONS

This application is a U.S. National Phase patent application of International Application No. PCT/JP2006/323621, with an international filing date of Nov. 27, 2006, which claims priority to Japanese Patent Application No. 342740/2005 filed on Nov. 28, 2005, all of which are incorporated herein by reference in their entirety.

TECHNICAL FIELD

The present invention relates to a percutaneous terminal, for example, for preventing bacterial infection at a living-body inserting section of a medical instrument to be placed in the body (medical device to be placed in the body), and relates to a medical instrument which prevents displacement inside the body. More specifically, the present invention relates to a medical instrument to be placed in the body such as a percutaneous terminal having a substrate thereof is flocked with fibers having bio-affinity, and thereby being able to adhere tightly to a living body. In addition, the present invention relates to a method for producing such a medical instrument to be placed in the body, and an apparatus for producing such a medical instrument to be placed in the body.

BACKGROUND ART

In recent years, medical instruments to be placed in the body such as percutaneous catheters have been used for medical treatment. For example, a percutaneous catheter is inserted inside a living body from outside the living body, in order to perform medical practices such as peritoneal dialysis. However, when the medical instrument to be placed in the body such as the percutaneous catheter is implanted in the living body, the medical instrument placed in the body is recognized as a foreign body by biological tissues. Therefore, the biological tissues and the medical instrument do not adhere tightly with each other. As a result, in the case of the percutaneous catheter for example, an epidermis sinks inwards along the catheter, so referred as a down-growth (phenomenon of which an epithelial sinks inwards along the surface of the catheter). The deepening of the down-growth causes insufficient disinfection. The insufficient disinfection creates an infection pathway for bacteria, which becomes a cause for inflammation of skin and other problems. Consequently, this causes a condition that in the end the medical instrument placed in the body has to be taken out from the body. For medical instruments to be placed in the body other than the percutaneous catheter, there is a problem that the medical instrument is moved in the body. In order to solve these problems, various medical instruments to be placed in the body have been proposed. The proposed medical instruments to be placed in the body are disclosed to have tight adhesiveness with the living body.

For example, intraperitoneal catheters and central venous catheters have a cuff member (Dacron cuff) made of Dacron nonwoven fabric in order to prevent bacterial infection and to fix the catheter to the living body (for example, see Patent Document 5). By implanting the Dacron cuff part under the skin, hyperplasia of hypodermic connective tissues occurs. Consequently, the catheter is firmly fixed. Because the catheter is securely fixed, the possibility of accidental evulsions is reduced. However, even with this catheter, the Dacron cuff and the biological tissues are not adhered together. Therefore, the bacterial infection is not completely prevented.

As another medical instrument to be placed in the body, a percutaneous terminal made of a highly bio-affinitive hydroxyapatite ceramics is proposed (see Non-Patent Document 2). However, the following problems exist in the arrangement of the disclosed conventional technique. In the arrangement of Non-Patent Document 2, the percutaneous terminal is formed from only a hydroxyapatite ceramics. Hydroxyapatite is a constituent of teeth and shows excellent bio-affinity with soft tissues, however the hydroxyapatite ceramics is hard and fragile. Therefore, the percutaneous terminal becomes hard. Consequently, a space may generate between the hydroxyapatite ceramics and the biological tissues when implanted inside the living body. This causes the problem of poor adhesiveness with the living body. Furthermore, if the percutaneous terminal is produced only with the hydroxyapatite ceramics, the percutaneous terminal becomes a large size. As such, various problems exist with the percutaneous terminal disclosed in Non-Patent Document 2, such that the percutaneous terminal is easily breakable, and discomfort is felt by patients due to the hardness of the percutaneous terminal when implanted inside the living body.

As another example, a method is proposed which modifies a highly bio-affinitive calcium phosphate on a surface of a base material of a medical device or a base material of a medical material, in order to allow tight adhesiveness with the living body. More specifically, for example, Patent Document 6 discloses a method which modifies the calcium phosphate on a surface of a base material of a medical component, by using sputtering ion beams. The medical component here is made of a polymer or the like. Patent Document 7 discloses a method which modifies the calcium phosphate on a surface of a base material made of glass, a ceramic calcium phosphate or the like, by soaking. Patent Document 8 discloses a method which precipitates the calcium phosphate on a surface of an inorganic biomaterial. Patent document 9 discloses a method which mechanically abuts the calcium phosphate or the like on a surface of a medical material by blasting or other methods. Patent document 10 discloses a method which modifies the calcium phosphate on a surface of a base material of a medical material such as an organic polymer or the like, by utilizing alternative soaking.

However, the calcium phosphate to be modified on the surface of the base material in the methods disclosed in Patent Documents 6 through 10 are all amorphous, which readily melts inside the living body. Therefore, the bio-affinity of the medical devices produced by using the medical materials described in Patent Documents 6 through 10 do not last for a long term inside the living body. As a result, the medical instruments are suitably used when the purpose of using the calcium phosphate is to melt the calcium phosphate in the body (for example, as a material to replace bones), however are not suitably used when the purpose of using the calcium phosphate is to keep the calcium phosphate inside the body for a long term (for example, the percutaneous terminal) or the like. In addition, the modifying method disclosed in Patent Documents 6 through 10 adhere the calcium phosphate to the base material either physically or electrostatically. This has the problem that adhering strength of the calcium phosphate is weak.

In order to attain the purpose of keeping the calcium phosphate inside the body for a long term, methods to modify a surface of a polymer base material with the calcium phosphate has been yearned for, and various proposals have been made. For example, methods such as the ones disclosed in Patent Documents 11 through 13 have been proposed. Patent Document 11 describes a method where ceramic porous particles made of hydroxyapatite are fixed on a surface of a polymer base material of an intraperitoneal catheter by using an adhesive, or by fusing the polymer base material. Patent Document 12 discloses a medical material in which a calcium phosphate such as hydroxyapatite is chemically bonded to a surface of a polymer base material. Patent Document 13 discloses a technique which coats an organic fiber aggregate or an inorganic fiber aggregate with a calcium phosphate compound, which is then jointed to an artificial trachea or the like.

However, if the porous particles made of highly bio-affinitive hydroxyapatite are adhered or fused on the surface of the catheter as described in Patent Document 11, the hydroxyapatite is applied directly to the catheter. This causes the problem that a part of the catheter where the hydroxyapatite is applied would differ in physical properties to the other parts of the catheter. In particular, if the porous particles made of hydroxyapatite are introduced to the catheter by fusing, the catheter would lose its physical properties and possibly break. If the hydroxyapatite is adhered directly to the catheter with an adhesive, problems arise such as the area of which the hydroxyapatite is exposed may decrease due to the soaking-in of the adhesive into the hydroxyapatite, or the hydroxyapatite may peel off from the catheter in case of insufficient adhering. If the fiber aggregate is coated with the calcium phosphate compound as described in Patent Document 13, the fiber which has not been coated with the calcium phosphate compound could possibly be exposed. In addition, this method requires to produce the fiber aggregate which is coated with the calcium phosphate and to join this coated fiber aggregate to a plastic body in advance. Thus, it is difficult to apply this method for a medical instrument and the like in complex shapes. Furthermore, Patent Document 13 forms the calcium phosphate by a liquid-phase precipitation method. The calcium phosphate formed by the liquid-phase precipitation method is amorphous. Therefore, the calcium phosphate readily melts inside the body. In addition, as described in paragraph [0012] of Patent Document 13, it is difficult to coat the calcium phosphate in a thickness of 1 μm or less. This is because it is industrially difficult to evenly coat the calcium phosphate in a thickness of 1 μm or less in a conventional liquid-phase precipitation method or other conventional methods. Furthermore, such thickness causes the calcium phosphate to readily melt inside the body.

In response to this, the inventors of the present invention independently developed a hydroxyapatite composite particle (see Patent Document 14). The hydroxyapatite composite particle is produced by chemically bonding a silk fibroin and the hydroxyapatite, and has high bio-affinity. Additionally, the inventors produced a percutaneous terminal which can adhere tightly to the living body, by adhering the hydroxyapatite composite particle to a surface of a substrate (see Non-Patent Document 3). The percutaneous terminal and a catheter provided with the percutaneous terminal can adhere to the living body far tighter compared to conventional percutaneous terminals.

A conventional and publicly known flocking method is referred as an electrostatic flocking or electrodeposition flocking. The flocking method is a processing method where short fibers (referred as 'pile flock' or 'pile') are orthogonally planted on a base material. An adhesive is applied to the base material in advance, and short fibers are planted by utilizing electrostatic attraction in a high voltage electrostatic field. The flocking method is not limited to simply planting short fibers, and various effects are attainable by selecting specific adhesives, short fibers, base materials and the like. Therefore, the method is utilized in a broad range of fields (see Non-Patent Document 1). For example, the flocking method is used in processing clothing and textile goods (for example, see Patent Documents 1 through 3). The flocking method is also used in processing makeup and cosmetic products (for example, see Patent Document 4) as well as processing elastic material such as rubber gloves (for example, see Patent Document 15). However, there have been no examples of which the flocking method is used for processing medical material. The technical idea itself of such process did not exist, to process flocking with short fibers on a surface of a medical instrument to be placed in the body such as a percutaneous catheter.

Non-Patent Document 1
"Shin Kobunshi Bunko 17 Furokku Kakou no Jissai (New Polymer Publishing 17 Facts of Flocking)", N. Iinuma, Polymer Publishing Inc., p. 1, published Aug. 1, 1979,
Non-Patent Document 2
H. AOKI, in "Medical Applications of Hydroxyapatite" (Ishiyaku EuroAmerica, Inc., 1994) p. 133-155
Non-Patent Document 3
Tsutomu Fruzono, PhD, Shoji Yasuda, M S, Tsuyoshi Kimura, PhD, Singo Kyotani, M D, Junzo Tanaka, PhD, Akio Kishida, PhD, "Nano-scaled hydroxyapatite/polymer composite IV. Fabrication and cell adhesion properties of a three-dimensional scaffold made of composite material with a silk fibroin substrate to develop a percutaneous device". J Artif Organs (2004) 7:137-144
Patent Document 1
Japanese Unexamined Patent Publication, Tokukaihei, No. 7-116557 (published May 9, 1995)
Patent Document 2
Japanese Unexamined Patent Publication, Tokuhyo, No. 2000-505845 (published May 16, 2000)
Patent Document 3
Japanese Unexamined Patent Publication, Tokukaihei, No. 6-141926 (published May 24, 1994)
Patent Document 4
Japanese Unexamined Patent Publication, Tokukai, No. 2003-38596 (published Feb. 12, 2003)
Patent Document 5
Japanese Unexamined Patent Publication, Tokukaihei, No. 8-206193 (published Aug. 13, 1996)
Patent Document 6
Japanese Unexamined Patent Publication, Tokukaihei, No. 8-56963 (published Mar. 5, 1996)
Patent Document 7
Japanese Unexamined Patent Publication, Tokukaihei, No. 7-306201 (published Nov. 21, 1995)
Patent Document 8
Japanese Unexamined Patent Publication, Tokukaisho, No. 63-270061 (published Nov. 8, 1988)
Patent Document 9
Japanese Unexamined Patent Publication, Tokukaihei, No. 7-303691 (published Nov. 21, 1995)
Patent Document 10
Japanese Unexamined Patent Publication, Tokukai, No. 2000-342676 (published Dec. 12, 2000)
Patent Document 11
Japanese Unexamined Patent Publication, Tokukaihei, No. 10-15061 (published Jan. 20, 1998)

Patent Document 12
Japanese Unexamined Patent Publication, Tokukai, No. 2001-172511 (published Jun. 26, 2001)
Patent Document 13
Japanese Unexamined Patent Publication, Tokukaihei, No. 06-327757 (published Nov. 29, 1994)
Patent Document 14
Japanese Unexamined Patent Publication, Tokukai, No. 2004-51952 (published Feb. 19, 2004)
Patent Document 15
U.S. Patent Application Publication No. 2004/0033334 (published Feb. 19, 2004)

DISCLOSURE OF INVENTION

[Problems to be Solved]

The percutaneous terminal produced by the inventors (Non-Patent Document 3) however is not one which the highly bio-affinitive hydroxyapatite composite particles are risen perpendicular to (or substantially perpendicular to) the surface of the substrate of the percutaneous terminal. A surface area of the hydroxyapatite composite particles is not extremely high with respect to a unit area of the substrate of the percutaneous terminal. Additionally, it is difficult to adhere the hydroxyapatite composite particles on the surface of the percutaneous terminal in the aforementioned method for percutaneous terminals in a complex shape, as like a percutaneous terminal including a body section and a flange section. The adhering of the hydroxyapatite composite particles to such percutaneous terminal is particularly difficult around a boundary of the body section and the flange section. This causes insufficient coating on the surface of the substrate of the percutaneous terminal with the hydroxyapatite composite particles. As such, sufficient adhesiveness with the living body would possibly be unattained even if the percutaneous terminal produced by the inventors is used.

The present invention is made in consideration of the problems, and an object thereof is to provide a percutaneous terminal which has high adhesiveness with the biological tissues (bioadhesiveness) and which can fix a medical tubing around a percutaneous section, and a medical device such as the medical tubing provided with the percutaneous terminal. In addition, another object of the present invention is to provide a method for producing such a percutaneous terminal which has the high bioadhesiveness, particularly a method which can coat a surface of a substrate of the percutaneous terminal with short fibers such as highly bio-affinitive hydroxyapatite composite particles and the like even for percutaneous terminals in complex shapes as like a percutaneous terminal including a body section and a flange section. Yet another object of the present invention is to provide an apparatus for producing such a percutaneous terminal which has the high bioadhesiveness. Furthermore, the present invention provides a medical instrument to be placed in the body, which has high bioadhesiveness, and is stably fixed inside the body. Another object of the present invention is to provide a method and an apparatus for producing such a medical instrument which has the high bioadhesiveness.

[Means to Solve the Problem]

The inventors of the present invention conducted diligent study in order to address the aforementioned problems. As a result, the inventors accomplished the present invention.

That is to say, in order to attain the objects, a percutaneous terminal according to the present invention is a percutaneous terminal for fixing a medical tubing inserted inside a living body, at an inserted position of the medical tubing, wherein: the percutaneous terminal has a substrate whose surface is flocked with bio-affinitive short fibers.

In addition, the percutaneous terminal according to the present invention is a percutaneous terminal for fixing a medical tubing inserted inside a living body, at an inserted position of the medical tubing, wherein: the percutaneous terminal has a substrate whose surface is coated with bio-affinitive short fibers, and a surface area of the short fibers which coat a unit area of the substrate of the percutaneous terminal is at least twice more than the unit area of the substrate of the percutaneous terminal.

The percutaneous terminal fixes a medical tubing inside the living body. The medical tubing extends from the inside of the living body to the outside of the living body. Examples of the medical tubing encompass: a catheter, an artificial vessel of a ventricular assist device (VAS) for sending or removing blood, and other medical tubing. More specifically, the percutaneous terminal fixes, at a percutaneous section (subcutaneous tissues and its vicinity) of the living body, the medical tubing inserted deep inside the living body via the biological tissues of the subcutaneous tissues and its vicinity.

The percutaneous terminal according to the present invention surface is one which has a substrate whose surface is flocked with bio-affinitive short fibers. Therefore, the bio-affinitive short fibers are risen perpendicular to or substantially perpendicular to the surface of the substrate of the percutaneous terminal. As a result, the surface area of the bio-affinitive short fibers which coat the unit area of the substrate of the percutaneous terminal remarkably increase with respect to the unit area of the substrate of the percutaneous terminal. The adhesiveness of the percutaneous terminal with the biological tissues thus improves, which enables to stably fix the medical device provided with the percutaneous terminal, such as the catheter and the like.

The percutaneous terminal according to the present invention is preferably arranged such that the bio-affinitive short fibers are made of a bio-affinitive ceramics, or a bio-affinitive ceramics composite in which a base material and the bio-affinitive ceramics are combined. The percutaneous terminal according to the present invention is further preferably arranged such that the bio-affinitive ceramics is calcium phosphate. In addition, the percutaneous terminal according to the present invention is preferably arranged such that the base material is a polymer base material.

The bio-affinitive ceramics indicate a ceramics which has affinity (adhesiveness) with the biological tissues. Particularly, the bio-affinitive ceramics indicate calcium phosphate sinter, and titanium oxide or the like which expresses adhesiveness with the living body due to processing a surface of a particle. That is, the bio-affinitive ceramics indicate at least one of the calcium phosphate and titanium oxide.

The bio-affinitive ceramics composite is a composite combining a bio-affinitive base material (polymer base material) with a bio-affinitive ceramics via chemical bonding, an adhesive or the like, and which possesses physical properties of both the base material and the bio-affinitive ceramics. The bio-affinitive ceramics has affinity with the biological tissues, and the base material and the substrate do not affect the living body even when implanted inside the living body. Additionally, it is preferable for the base material to be elastic.

According to the arrangement, the surface of the substrate of the percutaneous terminal is flocked with the short fibers made of the bio-affinitive ceramics composite. Therefore, a percutaneous terminal which has high adhesiveness with the biological tissues is provided, due to an achievement of good adhesion between the bio-affinitive ceramics composite and the biological tissues.

As the calcium phosphate has excellent affinity (adhesiveness) with the living body, the calcium phosphate is particularly preferred of the bio-affinitive ceramics. In particular, calcium phosphate sinter is preferred of the calcium phosphates. The following is a description of the calcium phosphate sinter. The calcium phosphate sinter is a noncrystalline (amorphous) calcium phosphate sintered in a high temperature (for example, in the temperature range of 800° C. to 1300° C.). A calcium phosphate composite is one which combines the bio-affinitive base material (polymer base material) and the calcium phosphate sinter via chemical bonding, an adhesive or the like. The calcium phosphate composite possesses the physical properties of both the base material and the calcium phosphate. The calcium phosphate sinter is excellent in affinity (adhesiveness) with the biological tissues, and the base material and the substrate do not affect the living body even when implanted inside the living body. Additionally, it is preferable for the base material to be elastic.

Of the bio-affinitive ceramics, the titanium oxide manifests adhesiveness and affinity with the living body by processing the surface of the titanium oxide. The following description deals with the titanium oxide.

The titanium oxide introduces a cationic functional group of an amino group or the like on a surface of a particle of the titanium oxide by chemical processing. The surface of the particles thus gains affinity with the biological tissues. A titanium oxide composite is a composite in which a bio-affinitive base material (polymer base material) is combined with a titanium oxide particle, via chemical bonding, an adhesive or the like. Thus, the titanium oxide composite possesses physical properties of both the base material and the titanium oxide particles. In other words, the titanium oxide includes the cationic functional group.

The surface-processed titanium oxide (particle) has excellent affinity (adhesiveness) with the biological tissues. Consequently, the base material and the substrate of the percutaneous terminal do not affect the living body even when implanted in the living body. Meanwhile, it is preferable for the base material and the substrate of the percutaneous terminal to be elastic.

According to the arrangement, the surface of the substrate of the percutaneous terminal is flocked with the bio-affinitive ceramics composite. Therefore, a percutaneous terminal which has high adhesiveness with the biological tissues is provided, due to an achievement of good adhesion between the bio-affinitive ceramics composite and the biological tissues. That is to say, the arrangement appropriately adheres the bio-affinitive ceramics and the biological tissues surrounding the medical tubing. Consequently, the medical tubing is appropriately fixed at the inserting position of the medical tubing, thereby suppressing the down-growth. The percutaneous terminal coated with the bio-affinitive ceramics composite uses the hard bio-affinitive ceramics and the elastic base material combined together. As a result, the percutaneous terminal is less likely to break compared to, for example, the percutaneous terminal made of hydroxyapatite. Furthermore, it is possible to reduce the stiffness felt by a patient when the percutaneous terminal is implanted inside the living body. In the arrangement, the bio-affinitive ceramics composite is coated on a substrate different to the medical tubing. Thus, the physical properties of the medical tubing do not deteriorate. That is to say, it is possible to provide a percutaneous terminal in which the medical tube is safely fixed inside the living body.

The bio-affinitive ceramics have high crystallinity and low solubility, compared to the noncrystalline ceramics. Therefore, the arrangement allows favorable use even for cases where the percutaneous terminal is used for the purpose of implanting the medical tubing for a long term.

The percutaneous terminal according to the present invention is preferably arranged such that the bio-affinitive short fibers have a columnar shape having a length in a major axis direction in a range of not less than 1 µm to less than 1 cm (preferably in a range of not less than 5 µm to less than 5 mm, most preferred in a range of not less than 50 µm to less than 1 mm), and a length in a minor axis direction in a range of not less than 1 nm to less than 1 mm (preferably in a range of not less than 10 nm to less than 0.5 mm, most preferred in a range of not less than 100 nm to less than 0.1 mm). If the length exceeds the preferred range, it is difficult for the short fibers to fly during the flocking process. It also becomes difficult to maintain the short fibers in a rising state once the surface of the percutaneous terminal is flocked. If the length is shorter than the preferred range, the surface area of the percutaneous terminal cannot be broadened. This makes it difficult to produce a percutaneous terminal with high bioadhesiveness. In the description of the present invention, the "major axis" of the short fiber denotes, for a cylindrical or a prismatic short fiber, a height of the short fiber with respect to a bottom surface thereof. The "minor axis" in the description of the present invention denotes as follows: if the bottom surface of the short fiber is substantially a circular shape, then a diameter of the circle; if the bottom surface of the short fiber is substantially an oval shape, then a minor axis of the oval; if the bottom surface of the short fiber is substantially a square shape, then a length of one side of the square; and if the bottom surface of the short fiber is substantially a rectangular shape, then a length of a short side of the rectangle.

The short fibers in the aforementioned shapes allow easy flocking on the surface of the substrate of the percutaneous terminal, and increase the surface area of the short fibers on the percutaneous terminal (e.g. calcium phosphate composite).

The percutaneous terminal according to the present invention is preferably arranged such that a flange section is provided on the substrate of the percutaneous terminal, for suppressing a movement of the substrate with respect to an inserting direction of the medical tubing.

According to the arrangement, a flange section is provided for suppressing movement of the substrate with respect to an extending direction of the medical tubing. This suppresses the movement of the medical tubing (the percutaneous terminal moving in an inward direction of the living body) even more, thereby suppresses the progression of the down-growth. The movement includes a parallel movement and a rotational movement. Therefore, when the percutaneous terminal is fixed inside the living body, the flange section fixes the position of the percutaneous terminal inside the living body, and also prevents the percutaneous terminal from rotating (including twisting of the percutaneous terminal inside the living body).

In addition, the percutaneous terminal according to the present invention is preferably arranged such that the flange section has a hole section provided thereon. According to the arrangement, a hole section is provided on the flange section. Thus, for example, when the percutaneous terminal is implanted inside the living body, the tissues inside the living body adhere with other tissues via the hole section. This thus enables to firmly fix the percutaneous terminal in its position.

The percutaneous terminal according to the present invention is preferably arranged such that the flange section is provided between one end of the substrate to the other end thereof, and the bio-affinitive short fibers (e.g. bio-affinitive ceramics composite) coat just an area from the one end of the substrate to an area including the flange section (or, an area from the one end to the flange section).

According to the arrangement, just an area from one end of the substrate to an area including the flange section is coated with the bio-affinitive short fibers (e.g. bio-affinitive ceramics, bio-affinitive ceramics composite). The bio-affinitive ceramics composite is not particularly only excellent in affinity (adhesiveness) with the biological tissues, but also shows good adhesiveness towards other cells outside the living body, for example saprophytes. Therefore, if the percutaneous terminal is implanted in a state where a part of the percutaneous terminal, which is the area not coated with the bio-affinitive ceramics composite, is exposed outside the living body, it is possible to prevent the adhering of the saprophytes on the percutaneous terminal. This is because the exposed part of the percutaneous terminal is not coated with the bio-affinitive ceramics composite. Namely, it is possible to implant the percutaneous terminal in the state where a part thereof is exposed outside the living body.

The percutaneous terminal according to the present invention is preferably arranged such that the flange section is provided in a predetermined angle with respect to the inserting direction of the medical tubing.

With the arrangement, it is possible to place the medical tubing exposed outside of the living body along the living body when the percutaneous terminal is implanted in the living body and the medical tubing is used therewith, by slanting the flange section with respect to the inserting direction of the medical tubing. This thus enables the medical tubing to be less obstructive outside the living body.

The flange section of the percutaneous terminal according to the present invention is required to be of a shape with consideration of the easiness in implantation to the living body and the manifestation of the high adhesiveness with the living body, when implanting the percutaneous terminal to the living body. More specifically, the percutaneous terminal to be implanted in the living body has two surfaces on the percutaneous terminal with respect to an extending direction of the medical tubing; a percutaneous terminal inner side surface that faces toward inside of the body, and a percutaneous terminal outer side surface that faces toward outside of the body.

The percutaneous terminal inner side surface denotes the surface of the percutaneous terminal to be implanted to the living body in the inserting direction side of the percutaneous terminal, from a center surface perpendicular to the extending direction of the medical tubing. The percutaneous terminal outer side surface denotes the surface of the percutaneous terminal to be implanted to the living body in the outer direction of the percutaneous terminal, from the center surface perpendicular to the extending direction of the medical tubing.

If the symmetry of the shape is low, the easiness in implantation differs depending on the implanting direction.

The medical tubing and the percutaneous terminal are implanted inside the body by the following processes: (i) an epithelium of an implanting section of the living body is partially incised; (ii) the medical tubing is punctured and indwelled in the living body; and (iii) the medical tubing is inserted inside the living body. Therefore, the flange section on the percutaneous terminal inner side surface is preferably shaped with a narrow tip so that it is easily inserted (implanted), and preferably has a broad area to attain an adhering surface with the living body. The end part of the flange section opposite to the inserting direction is preferably arranged such that the terminal has a broad area for adhering with the living body.

With the arrangement, the percutaneous terminal is easily inserted (implanted), and the adhesiveness with the body is improved.

The flange section of the percutaneous terminal according to the present invention is preferably arranged such that a plurality of hole sections is provided on the flange section in a constant proportion with respect to the surface area of the flange section.

With the arrangement, after implanting the percutaneous terminal, the biological tissues extend through the hole section. The extended biological tissues then adhere with the biological tissues on the other side of the flange section. The percutaneous terminal is thus fixed to the living body as though the flange section of the percutaneous terminal is sewn onto the living body with the tissues referred a thread. As such, it is possible to suppress the movement and rotation of the substrate with respect to the inserting direction of the medical tubing.

According to the arrangement, at least one part of the substrate is coated with multiple particle-shaped bio-affinitive ceramics composites. This increases the surface area of the bio-affinitive ceramics coated on the surface of the substrate, thereby enables to adhere the percutaneous terminal with the biological tissues more adequately.

The percutaneous terminal according to the present invention may be arranged integrally with the medical tubing.

According to the arrangement, the percutaneous terminal is arranged integrally with the medical tubing. This fixes the percutaneous terminal, which as a result prevents the movement of the catheter.

The following description deals with particularly the calcium phosphate sinter, of the bio-affinitive ceramics.

According to the arrangement, it is possible to increase a surface area of the calcium phosphate sinter coating the surface of the substrate, by having the calcium phosphate composite in a particle-shape or a fiber-shape.

The percutaneous terminal according to the present invention is preferably arranged such that the base material is a silk fibroin, polyester, or polytetrafiluoroethylene (hereafter referred as PTFE).

Particularly, the silk fibroin has high bio-affinity. According to the arrangement, a percutaneous terminal highly bio-affinitive with the living body is provided, by using the silk fibroin as the base material.

In order to attain the object, the percutaneous terminal according to the present invention is a percutaneous terminal for fixing a medical tubing inserted inside a living body, at an inserted position of the medical tubing, wherein: the percutaneous terminal has a substrate whose surface is coated with a silk fibroin on at least one part of the surface of the substrate.

The silk fibroin has high bio-affinity. Therefore, with the arrangement, it is possible to provide a percutaneous terminal with a high bioadhesiveness.

The medical tubing according to the present invention is arranged such that the medical tubing is provided with the percutaneous terminal. Thus, the movement of the medical tubing is prevented even when the medical tubing is implanted inside the living body.

A method according to the present invention for producing the percutaneous terminal is a method for producing a percutaneous terminal in which a surface of a substrate of the percutaneous terminal is flocked with bio-affinitive short fibers, the method comprising the steps of: arranging, between a first electrode plate and a second electrode plate, the substrate of the percutaneous terminal in which an adhesive is applied on the surface thereof; mounting the bio-affinitive short fiber on the second electrode plate; rotating the substrate of the percutaneous terminal; and applying a voltage to the first electrode plate and the second electrode plate, the first electrode plate and the substrate of the percutaneous terminal being electrically connected.

In addition, it is preferable that in the step of arranging, between the first electrode plate and the second electrode plate, the substrate of the percutaneous terminal in which an adhesive is applied on the surface thereof, the substrate of the percutaneous terminal is arranged between the first electrode plate and the second electrode plate in such that the first electrode plate and the second electrode plate make an angle or angles in a range of more than 0° to less than 90° with respect to an inserting direction in which a medical tubing is to be inserted to the percutaneous terminal.

According to the method, the bio-affinitive short fibers on the second electrode plate fly towards the first electrode plate due to a Coulomb force. Meanwhile, the substrate of the percutaneous terminal is arranged between the second electrode plate and the first electrode plate, and the bio-affinitive short fibers adhere on the surface of the substrate of the percutaneous terminal on which the adhesive is applied thereon. In addition, the first electrode plate and the substrate of the percutaneous terminal are electrically connected. Electromotive force thus generates to the bio-affinitive short fibers on the surface of the substrate of the percutaneous terminal, and effected by this, the bio-affinitive short fibers rise. Furthermore, the substrate of the percutaneous terminal is arranged and rotated so that the angle of the first electrode plate and the second electrode plate is 0° or more however less than 90°, with respect to the inserting direction of the medical tubing to the percutaneous terminal. This thus allows the even adhesion of the bio-affinitive short fibers, even if the percutaneous terminal is of a complex shape.

The method according to the present invention for producing the percutaneous terminal further preferably includes the step of moistening the bio-affinitive short fibers, in addition to the arrangement. The moistening of the bio-affinitive short fibers allows the short fibers itself to be readily charged. Consequently, the bio-affinitive short fibers readily fly. This attains the effect such that the surface of the substrate of the percutaneous terminal is easily flocked with the bio-affinitive short fibers.

The method according to the present invention for producing the percutaneous terminal is preferably arranged such that the bio-affinitive short fibers are made of a bio-affinitive ceramics, or a bio-affinitive ceramics composite in which a base material and the bio-affinitive ceramics are combined. In addition, the method according to the present invention is preferably arranged such that the bio-affinitive ceramics is calcium phosphate.

The method according to the present invention for producing the percutaneous terminal is preferably arranged such that the base material is a polymer base material. In addition, the method for producing the percutaneous terminal is preferably arranged such that the bio-affinitive short fibers have a columnar-shape or a spherical-shape having a length in a major axis direction in a range of not less than 1 µm to less than 1 cm (preferably in a range of not less than 5 µm to less than 5 mm, most preferred in a range of not less than 50 µm to less than 1 mm), and a length in a minor axis direction in a range of not less than 1 nm to less than 1 mm (preferably in a range of not less than 10 nm to less than 0.5 mm, most preferred in a range of not less than 100 nm to less than 0.1 mm).

The effect of the arrangement of the bio-affinitive short fibers and the base material in the method according to the present invention for producing the percutaneous terminal is as aforementioned in the description of the percutaneous terminal according to the present invention. Therefore, according to the method of the present invention, a percutaneous terminal with excellent bioadhesiveness is produced.

An apparatus according to the present invention for producing the percutaneous terminal is an apparatus for producing a percutaneous terminal in which a surface of a substrate of the percutaneous terminal is flocked with bio-affinitive short fibers, the apparatus including: a first electrode plate and a second electrode plate; and a rotation supporting section which includes a supporting section for supporting the substrate of the percutaneous terminal and a rotating section for rotating the supporting section, the second electrode plate being arranged under the first electrode plate, where a direction of gravity is denoted as downwards; the second electrode plate being arranged such that the bio-affinitive short fibers are mountable; the rotation supporting section being arranged so that the substrate of the percutaneous terminal, which substrate is supported by the supporting section is to be arranged between the first electrode plate and the second electrode plate; and the supporting section being electrically connected with the first electrode plate, and arranged electrically connectable with the substrate of the percutaneous substrate.

In the apparatus of the present invention, the rotation supporting section may be arranged such that the substrate of the percutaneous terminal, which substrate is supported by the supporting section is to be arranged between the first electrode plate and the second electrode plate, so that the first electrode plate and the second electrode plate make an angle or angles in a range of more than 0° however less than 90° with respect to an inserting direction in which a medical tubing is to be inserted to the percutaneous terminal.

The percutaneous terminal is produced as follows, for example, when the apparatus is used:
(i) The substrate of the percutaneous terminal in which the adhesive is applied on the surface thereof is fixed to the supporting section of the rotation supporting section.
(ii) The bio-affinitive short fibers are mounted on the second electrode plate.
(iii) The substrate of the percutaneous terminal is rotated due to the rotating section of the rotation supporting section.
(iv) A voltage is applied to the first electrode plate and the second electrode plate.

By following each of the steps, firstly the bio-affinitive short fibers on the second electrode plate fly towards the first electrode plate due to the Coulomb force. Meanwhile, the substrate of the percutaneous terminal is arranged between the second electrode plate and the first electrode plate, and the bio-affinitive short fibers adhere on the surface of the substrate of the percutaneous terminal on which the adhesive is applied thereon. In addition, the first electrode plate and the substrate of the percutaneous terminal are electrically connected. The electromotive force thus generates to the bio-affinitive short fibers on the surface of the substrate of the percutaneous terminal, and effected by this, the bio-affinitive short fibers rise. Furthermore, the substrate of the percutaneous terminal is arranged and rotated so that the first electrode plate and the second electrode plate make an angle or angles in a range of 0° or more however less than 90°, with respect to the inserting direction in which the medical tubing is to be inserted to the percutaneous terminal. This thus allows the even adhesion of the bio-affinitive short fibers, even if the percutaneous terminal is of a complex shape.

The apparatus according to the present invention for producing the percutaneous terminal further preferably includes moistening means for moistening the bio-affinitive short fibers. According to the arrangement, the bio-affinitive short fibers may be moistened. The bio-affinitive short fibers are thus readily charged, which allows the bio-affinitive short fibers to readily fly. Thus, the surface of the substrate of the percutaneous terminal is readily flocked with the bio-affinitive short fibers.

The apparatus according to the present invention for producing the percutaneous terminal may further include a container for containing at least the first electrode plate, the second electrode plate and the supporting section; and a humidity controlling section for controlling humidity inside the container. According to the arrangement, the humidity of the bio-affinitive short fibers is more thoroughly controlled, and the surface of the substrate of the percutaneous terminal is more easily flocked with the bio-affinitive short fibers. The relative humidity inside the container controlled by the humidity controlling section is preferably in a range of 10 to less than 100%, is further preferable in a range of 20 to less than 95%, and is most preferred in a range of 30 to less than 90%. If the humidity exceeds the preferred range, excess moisture is attached to the bio-affinitive short fibers. This makes it difficult for the short fibers to fly. If the humidity is under the preferred range, the short fibers itself do not readily charge. This also makes it difficult for the short fibers to fly.

In order to attain the objects, a medical instrument to be placed in the body according to the present invention is a medical instrument to be placed inside a living body; and the medical instrument to be placed in the body has a substrate whose surface is flocked with bio-affinitive short fibers.

In addition, the medical instrument to be placed in the body according to the present invention is a medical instrument to be placed inside a living body; the medical instrument to be placed in the body has a substrate whose surface is coated with bio-affinitive short fibers; and a surface area of the short fibers which coat a unit area of the substrate of the medical instrument to be placed in the body is at least twice more than the unit area of the substrate of the medical instrument to be placed in the body.

The medical instrument to be placed in the body according to the present invention is one which the surface of the substrate is flocked with the bio-affinitive short fibers, therefore the bio-affinitive short fibers are risen perpendicular to or substantially perpendicular to the surface of the substrate. As a result, the surface area of the bio-affinitive short fibers coated on the unit area of the substrate of the medical instrument to be placed in the body significantly improves with respect to the unit area of the substrate of the medical instrument to be placed in the body. This improves the adhesiveness of the medical instrument to be placed in the body with the biological tissues, thus allows stable fixing of the medical instrument to be placed in the body.

The medical instrument to be placed in the body according to the present invention is preferably arranged such that the bio-affinitive short fibers are made of a bio-affinitive ceramics, or a bio-affinitive ceramics composite in which a base material and the bio-affinitive ceramics are combined. In addition, the medical instrument to be placed in the body according to the present invention is preferably arranged such that the bio-affinitive ceramics is calcium phosphate, particularly calcium phosphate sinter of the calcium phosphates. In addition, the medical instrument to be placed in the body according to the present invention is preferably arranged such that the base material is a polymer base material.

Of the bio-affinitive ceramics, titanium oxide manifests adhesiveness and affinity with the living body by processing the surface of the substrate.

The surface-processed titanium oxide (particle) is excellent in bio-affinity (adhesiveness) with the biological tissues, and the base material and the substrate of the medical instrument to be placed in the body do not affect the living body when implanted to the living body. In addition, it is preferable for the base material and the substrate to be elastic.

According to the arrangement, the surface of the substrate of the medical instrument to be placed in the body is flocked with the short fibers made of the bio-affinitive ceramics composite. Thereby, due to an achievement of good adhesion between the bio-affinitive ceramics composite and the biological tissues by the flocked substrate of the medical instrument to be placed in the body, a medical instrument to be placed in the body which has high adhesiveness with biological tissues is provided. Meanwhile, it is preferable for the base material and the substrate to be elastic.

According to the arrangement, the surface of the substrate of the medical instrument to be placed in the body is flocked with the short fibers made of the bio-affinitive ceramics composite. Therefore, the medical instrument to be placed in the body which has high adhesiveness with the biological tissues is provided, due to an achievement of good adhesion between the bio-affinitive ceramics composite and the biological tissues. That is to say, the aforementioned arrangement appropriately adheres the bio-affinitive ceramics and the tissues in contact with the living body contact surface of the medical instrument to be placed in the body. Consequently, the position of the medical instrument to be placed in the body is appropriately fixed, which enables the suppression of the down-growth. The medical instrument to be placed in the body coated with the bio-affinitive ceramics composite uses the hard bio-affinitive ceramics and the elastic base material combined together. As a result, the medical instrument to be placed in the body is less likely to break compared to the medical instrument to be placed in the body made of the hydroxyapatite. Furthermore, it is possible to reduce the stiffness felt by a patient when the medical instrument to be placed in the body is implanted to the living body. With the arrangement, that is to say, it is possible to provide a percutaneous terminal in which the medical tube is safely fixed inside the living body.

The bio-affinitive ceramics have high crystallinity and low solubility, compared to the noncrystalline ceramics. Therefore, the aforementioned arrangement allows favorable use even for cases where the medical instrument to be placed in the body is used for the purpose of implanting the medical tubing for a long term.

The medical instrument to be placed in the body according to the present invention is preferably arranged such that the bio-affinitive short fibers have a columnar-shape having a length in a major axis direction in a range of not less than 1 µm to less than 1 cm (preferably in a range of not less than 5 µm to less than 5 mm, most preferred in a range of not less than 50 µm or more to less than 1 mm), and a length in a minor axis direction in a range of 1 nm to less than 1 mm (preferably in a range of not less than 10 nm to less than 0.5 mm, most preferred in a range of not less than 100 nm to less than 0.1 mm). If the length exceeds the preferred range, it is difficult for the short fibers to fly during the flocking process. It is also difficult to maintain the short fibers in a risen state once the surface of the medical instrument to be placed in the body is flocked. If the length is shorter than the preferred range, the surface area of the medical instrument to be placed in the body cannot be broadened. This makes it difficult to produce a medical instrument to be placed in the body with high bioadhesiveness.

The short fibers in the aforementioned shapes allow easy flocking on the surface of the substrate of the medical instrument to be placed in the body, and increase the surface area of the short fibers on the medical instrument to be placed in the body (e.g. calcium phosphate composite).

The medical instrument to be placed in the body according to the present invention is preferably a medical instrument selected from the group consisting of an artificial vessel, a stent, a stent graft, an artificial trachea, a pace maker, an artificial heart and an access port.

These medical instruments particularly require suppression of disposition in the living body. The medical instrument to be placed in the body such as the artificial vessel has excellent adhesiveness with the biological tissues. This is because the medical instrument to be placed in the body is flocked with bio-affinitive short fibers on the surface of the substrate of the medical instrument. Therefore, the disposition inside the living body is suppressed.

In order to attain the object, a method according to the present invention for producing the medical instrument to be placed in the body is a method for producing a medical instrument to be placed in the body in which a surface of a substrate of the medical instrument to be placed in the body is flocked with bio-affinitive short fibers, the method comprising the steps of: arranging, between a first electrode plate and a second electrode plate, the substrate of the medical instrument to be placed in the body in which an adhesive is applied on the surface thereof; mounting the bio-affinitive short fibers on the second electrode plate; rotating the substrate of the medical instrument to be placed in the body; and applying a voltage to the first electrode plate and the second electrode plate, the first electrode plate and the substrate of the medical instrument to be placed in the body being electrically connected.

According to the method for producing the medical instrument to be placed in the body, the bio-affinitive short fibers on the second electrode plate fly towards the first electrode plate due to the Coulomb force. The medical instrument to be placed in the body is arranged between the second electrode plate and the first electrode plate, and the bio-affinitive short fibers adhere on the surface of the substrate of the medical instrument to be placed in the body in which the adhesive is applied thereon. In addition, the first electrode plate and the substrate of the medical instrument to be placed in the body are electrically connected. The electromotive force thus generates to the bio-affinitive short fibers on the surface of the substrate of the medical instrument to be placed in the body, and effected by this, the bio-affinitive short fibers rise.

The method according to the present invention for producing the medical instrument to be placed in the body further preferably includes the step of moistening the bio-affinitive short fibers. The moistening of the bio-affinitive short fibers allows the short fibers itself to be readily charged. Consequently, the bio-affinitive short fibers readily fly. This attains the effect such that the surface of the substrate of the medical instrument to be placed in the body is easily flocked with the bio-affinitive short fibers.

The method according to the present invention for producing the medical instrument to be placed in the body is preferably arranged such that the bio-affinitive short fibers are made of a bio-affinitive ceramics, or a bio-affinitive ceramics composite in which a base material and the bio-affinitive ceramics are combined. In addition, the method according to the present invention is preferably arranged such that the bio-affinitive ceramics is calcium phosphate.

The method according to the present invention for producing the medical instrument to be placed in the body is preferably arranged such that the base material is a polymer base material. In addition, the method for producing the medical instrument to be placed in the body is preferably arranged such that the bio-affinitive short fibers have a columnar-shape having a length in a major axis direction in a range of not less than 1 µm to less than 1 cm (preferably in a range of not less than 5 µm to less than 5 mm, most preferred in a range of not less than 50 µm to less than 1 mm), and a length in a minor axis direction in a range of not less than 1 nm to less than 1 mm (preferably in a range of not less than 10 nm to less than 0.5 mm, most preferred in a range of not less than 100 nm to less than 0.1 mm).

The effect of the arrangement of the bio-affinitive short fibers and the base material in the method according to the present invention for producing the medical instrument to be placed in the body is as aforementioned in the description of the medical instrument to be placed in the body according to the present invention. Therefore, according to the method according to the present invention for producing the medical instrument to be placed in the body, a medical instrument to be placed in the body with excellent bioadhesiveness is produced.

An apparatus according to the present invention for producing the medical instrument to be placed in the body is an apparatus for producing a medical instrument to be placed in the body in which a surface of a substrate of the medical instrument to be placed in the body is flocked with bio-affinitive short fibers, the apparatus including: a first electrode plate and a second electrode plate; and a rotation supporting section which includes a supporting section for supporting the substrate of the medical instrument to be placed in the body and a rotating section for rotating the supporting section, the second electrode plate being arranged under the first electrode plate, where a direction of gravity is denoted as downwards; the second electrode plate being arranged such that the bio-affinitive short fibers are mountable; the rotation supporting section being arranged so that the substrate of the medical instrument to be placed in the body, which substrate is supported by the supporting section is to be arranged between the first electrode plate and the second electrode plate; and the supporting section being electrically connected with the first electrode plate, and arranged electrically connectable with the substrate of the medical instrument to be placed in the body.

The medical instrument to be placed in the body is produced as follows, for example, when the aforementioned apparatus is used:

(i) The substrate of the medical instrument to be placed in the body in which the adhesive is applied on the surface thereof is fixed to the supporting section of the rotation supporting section.

(ii) The bio-affinitive short fibers are mounted on the second electrode plate.

(iii) The substrate of the medical instrument to be placed in the body is rotated due to the rotating section of the rotation supporting section.

(iv) A voltage is applied to the first electrode plate and the second electrode plate.

By following each of the steps, firstly the bio-affinitive short fibers on the second electrode plate fly towards the first electrode plate due to the Coulomb force. Meanwhile, the medical instrument to be placed in the body is arranged between the second electrode plate and the first electrode plate, and the bio-affinitive short fibers adhere on the surface of the substrate of the medical instrument to be placed in the body in which the adhesive is applied thereon. In addition, the first electrode plate and the substrate of the medical instrument to be placed in the body are electrically connected. The electromotive force thus generates to the bio-affinitive short fibers on the surface of the substrate of the medical instrument to be placed in the body, and effected by this, the bio-affinitive short fibers rise.

The apparatus according to the present invention for producing the medical instrument to be placed in the body further preferably includes moistening means for moistening the bio-affinitive short fiber. According to the arrangement, the bio-affinitive short fibers may be moistened. The bio-affinitive short fibers are thus readily charged. This allows the bio-affinitive short fibers to fly more easily, and the surface of the substrate of the medical instrument to be placed in the body, is flocked with the bio-affinitive short fibers more easily.

The apparatus according to the present invention for producing the medical instrument to be placed in the body may further include a container for containing at least the first electrode plate, the second electrode plate and the supporting section; and a humidity controlling section for controlling humidity inside the container.

According to the arrangement, the humidity of the bio-affinitive short fibers is more thoroughly controlled, and the surface of the substrate of the medical instrument to be placed in the body is more easily flocked with the bio-affinitive short fibers. The relative humidity inside the container controlled by the humidity controlling section is preferably in a range of 10 to less than 100%, is further preferable in a range of 20 to less than 95%, and is most preferred in a range of 30 to less than 90%. If the humidity exceeds the preferred range, excess moisture is attached to the bio-affinitive short fibers. This makes it difficult for the short fibers to fly. If the humidity is under the preferred range, the short fibers itself do not readily charge. This also makes it difficult for the short fibers to fly.

Effect

The percutaneous terminal according to the present invention is one which the percutaneous terminal has a substrate whose surface is flocked with the bio-affinitive short fibers. Therefore, the bio-affinitive short fibers are risen perpendicular to or substantially perpendicular to the surface of the substrate of the percutaneous terminal. As a result, the surface area of the bio-affinitive short fiber which coat the unit area of the substrate of the percutaneous terminal remarkably increases with respect to the unit area of the substrate of the percutaneous terminal. The adhesiveness of the percutaneous terminal and the biological tissues thus improves, which enables to stably fix medical devices such as a catheter having the percutaneous terminal in the living body, by the percutaneous terminal according to the present invention.

According to the method and the apparatus according to the present invention for producing the percutaneous terminal, it is possible to produce a percutaneous terminal as like the aforementioned. Therefore, according to the method and the apparatus according to the present invention, a percutaneous terminal which has high adhesiveness with the biological tissues is provided.

The medical instrument to be placed in the body according to the present invention is one which the percutaneous terminal has a substrate whose surface is flocked with the bio-affinitive short fibers. Therefore, the bio-affinitive short fibers are risen perpendicular to or substantially perpendicular to the surface of the substrate of the percutaneous terminal. As a result, the surface area of the bio-affinitive short fibers coating the unit area of the substrate of the percutaneous terminal remarkably increases with respect to the unit area of the substrate of the percutaneous terminal. The adhesiveness of the percutaneous terminal and the biological tissues thus improves, which enables to stably fix medical devices such as a catheter having the percutaneous terminal in the living body, by the percutaneous terminal according to the present invention.

EXPLANATION OF REFERENCE NUMERALS

Figure 1:
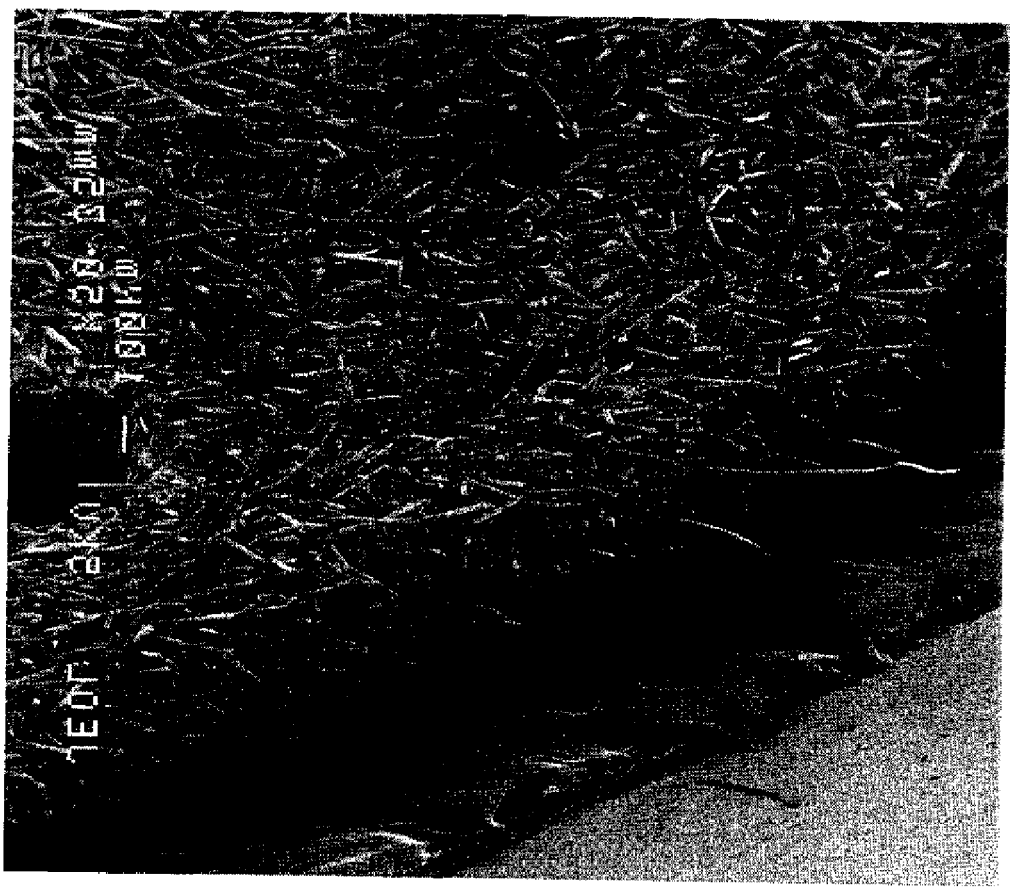
FIG. 1 is a scanning electronography of a percutaneous terminal produced in Example 1.

| | |
|---|---|
| 1 | Flocking device |
| 2 | First electrode plate |
| 3 | Second electrode plate |
| 4 | Humidity controlling section 4 |
| 5 | Container 5 |
| 6a | Supporting section |
| 6b | Rotating section |
| 6 | Rotation supporting section |
| 10 | Short fibers |
| 11 | Substrate of a percutaneous terminal |

| | |
|---|---|
| 100 | Percutaneous terminal |
| 101 | Body section |
| 102 | Flange section |
| 103 | Hole section |

BEST MODE FOR CARRYING OUT THE INVENTION

One embodiment of the present invention is described below. The present invention however is not limited to this.

[1. Percutaneous Terminal According to the Present Invention]

A percutaneous terminal according to the present invention is a percutaneous terminal for fixing, at an inserted position of the medical tubing, a medical tube inserted inside a living body, the percutaneous terminal having a substrate having a surface flocked with bio-affinitive short fibers.

"Bio-affinitive short fibers" denote short fibers made from a material compatible with biological tissues, and which has no harmful effect to the living body when implanted to the living body. The material is not particularly limited, provided that the material is bio-affinitive, and examples of the materials encompass the aforementioned bio-affinitive ceramics, a bio-affinitive ceramics composite later described, and other bio-affinitive materials.

The following description deals with the "bio-affinitive ceramics" and the "bio-affinitive ceramics composite" as an example of the bio-affinitive short fibers. A calcium phosphate sinter is given as one example of the "bio-affinitive ceramics", and a bio-affinitive ceramics composite ("calcium phosphate composite") produced by using the calcium phosphate sinter is given as one example of the "bio-affinitive ceramics composite". However, the present invention is not limited to this. The description of the calcium phosphate as the bio-affinitive ceramics can be fully cited for the description of titanium oxide as the bio-affinitive ceramics.

(Calcium Phosphate Sinter)

The following description deals with the calcium phosphate sinter. The calcium phosphate sinter (also referred as a calcium phosphate ceramics) indicates a calcium phosphate with high crystallinity compared to an amorphous (noncrystalline) calcium phosphate. More specifically, the calcium phosphate sinter is obtained by sintering the amorphous (non-crystalline) calcium phosphate. The calcium phosphate sinter has, on a surface of the calcium phosphate sinter, at least one of calcium ions ($Ca^{2+}$), phosphate ions ($PO_4^{2-}$) and hydroxide ions ($OH^-$).

The calcium phosphate sinter is known for its high bio-affinity. Detailed examples of the calcium phosphate sinter encompass: hydroxyapatite ($Ca_{10}(PO_4)_6(OH)_2$), tricalcium phosphate (β(α)-tricalcium phosphate ($Ca_3(PO_4)_2$), calcium metaphosphate ($Ca(PO_3)_2$), octacalcium phosphate (OCP), $Ca_{10}(PO_4)_6F_2$, $Ca_{10}(PO_4)_6Cl_2$, and other sinters. Calcium phosphate which form the calcium phosphate sinter may be artificially produced in a publicly known producing method such as a wet method, a dry method, a hydrolysis method or a hydrothermal method, or may be one from a nature source obtained from bones, teeth and other natural material. The calcium phosphate sinter may include a compound or the like in which part of the hydroxide ions and/or phosphate ions of calcium phosphate is substituted with carbonate ions, chloride ions, fluoride ions, or other ions.

Calcium phosphate has high crystallinity and low solubility in the living body compared to noncrystalline calcium phosphate. Thus, calcium phosphate is suitably used even for implanting the percutaneous terminal to the living body for a long term.

On one of a crystal face of the calcium phosphate sinter, at least phosphate ion or calcium ion exists. More specifically, the existing ions differ depending on the crystal face of calcium phosphate, and calcium ions and phosphate ions exist on different crystal faces. If hydroxide ions are included in the calcium phosphate sinter, hydroxide ions exist on at least one of the crystal faces where the calcium ion or phosphate ion exists.

The following describes a producing method of the calcium phosphate sinter. The calcium phosphate sinter according to the embodiment is obtained by sintering amorphous calcium phosphate. More specifically, the calcium phosphate sinter is obtained by sintering calcium phosphate for a predetermined time in a temperature range of 800° to 1300°. The crystallinity of calcium phosphate is improved by sintering calcium phosphate, and which for example decreases the solubility when induced inside the living body. The degree of crystallinity of the calcium phosphate sinter is measured by an X-ray diffraction method (XRD). More specifically, a narrower half width of a peak which indicates each of the crystal faces of the calcium phosphate composite indicates a higher crystallinity of the calcium phosphate sinter.

A minimum sintering temperature for sintering calcium phosphate is preferably 800° C. or higher, further preferably 900° C. or higher, and particularly preferred as 1000° C. or higher. If the sintering temperature is lower than 800° C., the sintering may become insufficient. A maximum sintering temperature is preferably not higher than 1300° C., further preferably not higher than 1250° C., and particularly preferred as not higher than 1200° C. If the sintering temperature is higher than 1300° C., direct chemical bonding with a functional group possessed by a base material later described may become difficult to perform. As such, by having the sintering temperature within the aforementioned range, the calcium phosphate sinter is produced which unreadily melts inside the living body (which has high crystallinity) and which can chemically bond directly with the functional group possessed by the base material. A sintering time is not particularly limited, and may be set as appropriate.

For example, if hydroxyapatite sinter or β(α)-tricalcium phosphate is used as the material to form the calcium phosphate sinter, the calcium phosphate sinter would be suitable for medical material. This is because the hydroxyapatite sinter and the β(α)-tricalcium phosphate have excellent affinity with the living body and excellent stability in the living body environment. In addition, the hydroxyapatite sinter scarcely melts inside the living body. Therefore, if a calcium phosphate composite is produced with the hydroxyapatite sinter, the bio-affinity is maintained in the living body for a long term.

The calcium phosphate sinter is more preferably particle-shaped, and further preferred as a fine particle. More specifically, if the calcium phosphate sinter is of a spherical shape, the diameter thereof is preferably in a range of 10 nm to 100 μm, and is further preferable in a range of 50 nm to 10 μm. The use of the fine particles of the calcium phosphate sinter in the above range allows the adding of elasticity to the obtained percutaneous terminal. Note that in the description of the present invention, "A to B" denotes "A or more, B or less".

(Base Material)

A base material according to the present embodiment is more preferably a polymer base material, is further preferably a medical polymer, and is particularly preferrably an organic polymer. Detailed examples of the base material encompass:

synthetic polymers such as silicone polymer (may also be silicone rubber), polyethylene glycol, polyalkylene glycol, polyglycolic acid, polylactic acid, polyamide, polyurethane, polysulfone, polyether, polyether-ketone, polyamine, polyurea, polyimide, polyester, polyethylene, polypropylene, polytetrafluoroethylene, polyacrylic acid, polymethacrylic acid, polymethylmethacrylate, polyacrylonitrile, polystyrene, polyvinyl alcohol, and polyvinyl chloride; polysaccharides such as cellulose, amylose, amylopectin, chitin, and chitosan; mucopolysaccharides and the like such as polypeptides including collagen and the like, hyaluronic acid, chondroitin, and chondroitin sulfuric acid; and natural polymers such as a silk fibroin. Of the above base materials, silicone polymer, polyurethane, polytetrafluoroethylene or silk fibroin are suitably used, due to the excellent characteristic of long-lasting stability, strength, flexibility and the like in these base materials. The base material may also be one combining, for example, the organic polymer and the inorganic material.

The surface of the base material according to the present embodiment preferably has a functional group which can chemically bond with the calcium phosphate sinter itself. The functional group possessed by the surface of the base material allows chemical bonding of the base material with the calcium phosphate sinter without the need of a chemical process to the calcium phosphate sinter beforehand. The following describes a case where a functional group chemically bondable with the calcium phosphate sinter is introduced on the surface of the base material.

If the calcium phosphate sinter is the hydroxyapatite sinter, the hydroxyapatite sinter is chemically bondable with at least one of the functional groups selected from the group consisting of an isocyanate group and an alcoxysilyl group. That is to say, the base material and the hydroxyapatite sinter are chemically bondable if the base material has at least one functional group selected from the group consisting of isocyanate group and alcoxysilyl group. The "alcoxysilyl group" denotes groups including Si—OR. That is to say, in the present embodiment, the alcoxysilyl group encompasses —Si—OR, =Si—(OR)$_2$, —Si—(OR)$_3$, and the like. The "=" and the "≡" of the —Si—OR and the =Si—(OR)$_2$ not only indicate a triple bond and a double bond, respectively, but also each "hand" of the bonding may bond with different groups. Therefore, for example, —SiH—(OR)$_2$, —SiH$_2$—(OR), and the like are also included in the alcoxysilyl group. Note that the R of the Si—OR denotes an alkyl group or hydroxide.

The functional group possessed by the surface of the base material may be a functional group possessed by the base material itself, or may be one introduced by modifying the base material by publicly known means such as an acid/alkaline treatment, a corona discharging, a plasma radiation, or a surface graft polymerization processed on the surface of the base material.

In order to introduce the functional group, an active group may be introduced to the base material and used for introducing the functional group.

A shape of the base material is not particularly limited, and may be of a sheet-shape, a particle-shape, a fiber-shape, or any other shape, provided that the shape can be arranged as short fibers at the end. Specifically, if the base material is sheet-shaped, the base material can be cut into the desired short fiber shape after the base material is bonded with the calcium phosphate sinter. The base material may be bonded with the calcium phosphate sinter following the shape formation of the base material in the desired short fiber shape. In this case, the shape of the base material is preferred to be a remarkably smaller columnar shape (for example a cylindrical shape) than the size of a substrate later described. More specifically, if the shape of the material is a columnar shape, the length in the major axis direction is preferably in a range of not less than 1 µm to less than 1 cm (preferably in a range of not less than 5 µm to less than 5 mm, most preferred in a range of not less than 50 µm to less than 1 mm), and the length in the minor axis direction is preferably in a range of not less than 1 nm to less than 1 mm (preferably in a range of not less than 10 nm to less than 0.5 mm, most preferred in a range of not less than 100 nm to less than 0.1 mm). In the description of the present invention, the "major axis of the columnar shape" denotes a height with respect to a bottom surface of the columnar shape, for a cylindrical or a prismatic short fiber. On the other hand, "minor axis of the short fiber" in the description of the present invention denotes the lengths as follows: if the bottom surface shape of the short fiber is substantially a circle, a diameter of the circle; if the bottom surface shape of the short fiber is substantially an oval, a minor axis of the oval; if the bottom surface shape of the short fiber is substantially a square, a length of one side of the square; and if the bottom surface shape of the short fiber is substantially a rectangle, a length of a short side of the rectangle. The amount of the calcium phosphate sinter bonded to the base material is increased by using the base material in the shapes in the aforementioned range. This enables to obtain a further high bio-affinitive calcium phosphate composite.

(Calcium Phosphate Composite)

The calcium phosphate composite is attained by bonding the functionalized base material with the calcium phosphate sinter. The base material and the calcium phosphate may be bonded via an adhesive, or by chemical bonding. Detailed examples of the adhesive used when bonding the base material and the calcium phosphate encompass: a silicone type adhesive, polyethylene-vinyl acetate copolymer, polyester, nylon, urethane elastomer, vinyl acetate, acrylic resin, and the like. It is preferable to bond the base material and the calcium phosphate by chemical bonding, since the bonding of the base material and calcium phosphate is firmer.

The base material and the calcium phosphate sinter may be chemically bonded by, for example, (i) a method where a functional group chemically bondable with the calcium phosphate sinter is introduced to the base material, and the functional group and the base material which induces the calcium phosphate sinter are reacted with each other; or (ii) inducing to the calcium phosphate sinter a reactive functional group chemically bondable with the base material, and reacting the calcium phosphate sinter introducing the reactive functional group and the base material with each other.

If the calcium phosphate composite according to the present embodiment is, for example, a hydroxyapatite composite, the hydroxyapatite sinter is chemically bonded on the surface of the base material. More specifically, a hydroxyl group (—OH) existing in the hydroxyapatite sinter and an isocyanate group (—NCO) or an alcoxysilyl group possessed by the base material or a surface modified linker are chemically bonded, directly. If the alcoxysilyl group of the base material is —Si—=(OR)$_3$, a bonding as shown in chemical formula I exists between the hydroxyapatite sinter and the base material:

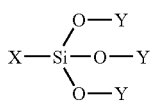

$$X-\underset{\underset{O-Y}{|}}{\overset{\overset{O-Y}{/}}{Si}}-O-Y \qquad (1)$$

where X and Y each denote either the base material or the hydroxyapatite sinter exchangeably such that if X is the base material, Y is the hydroxyapatite sinter, and vise versa.

A silicon atom (Si) of the chemical formula (1) is a part of the alcoxysilyl group. More specifically, the silicon atom may be a part of a surface-modified graft chain of the base material, or a part of the alcoxysilyl group contained in the polymer chain. The oxygen atom (O) of the chemical formula (1) is a part of the alcoxysilyl group or a part of the hydroxyl group included in the hydroxyapatite sinter. The X and Si of the chemical formula (1) may be bonded by the polymer chain or a monomeric chain, or may be bonded directly.

If the functional group is the isocyanate group, the hydroxyapatite sinter and the base material are chemically bonded by urethane bonding.

The calcium phosphate composite used in the present embodiment is preferably obtained by (i) introducing to the base material the functional group chemically bondable with the calcium phosphate sinter, and (ii) reacting the calcium phosphate sinter with the functional group. More specifically, the calcium phosphate composite is further preferably arranged such that a base material which possesses at least one of a functional group selected from the group consisting of the isocyanate group, the alcoxysilyl group, and a 4-methacryloxyethyl trimellytate anhydrite group, is chemically bonded with the calcium phosphate sinter (preferably the hydroxyapatite sinter). By introducing to the base material a functional group chemically bondable with the calcium phosphate sinter, and reacting the functional group with the calcium phosphate sinter, the calcium phosphate composite is produced without the need of chemically processing the calcium phosphate sinter beforehand. Thus, the calcium phosphate composite is obtained without losing the bio-affinity of the calcium phosphate sinter.

It is preferable for the calcium phosphate composite according to the present embodiment to have on the base material a bonding amount (surface coverage) of the calcium phosphate sinter of 5% by weight or more. The bonding amount is more preferably 7% by weight or more, further preferably 10% by weight or more, and particularly preferable as 12% by weight or more. The calcium phosphate composite shows high bioadhesiveness, for example when used for medical material such as the percutaneous terminal, by having the bonding amount as 5% by weight or more.

The calcium phosphate composite according to the present embodiment may be arranged such that the calcium phosphate sinter and the base material are chemically bonded by ionic interaction. The description of this is as below.

In the case where the calcium phosphate sinter chemically bonds with the base material due to ionic interaction, an ionized functional group exists on the surface of the base material in the calcium phosphate of the present embodiment. When the ionized functional group exists on the surface of the base material, the calcium phosphate composite (calcium phosphate composite) is formed by chemically bonding the ionized functional group and ions of the calcium phosphate sinter itself effected by the ionic interaction.

The ionized functional group is classified into an acidic functional group and a basic functional group.

Detailed examples of the acidic functional group encompass: $-COO^-$, $-SO_3^{2-}$, $-SO_3^-$, $-O^-$, $R_2NC(S)_2^-$, and the like. Detailed examples of the basic functional group encompass: $-NH^{3+}$, ethylene diamine, pyridine, and the like. That is to say, the aforementioned acidic functional group or the basic functional group exists on the surface of the base material. Note that the R of the $R_2NC(S)_2^-$ denotes an alkyl group.

The ionized functional group may be any functional group, provided that the functional group ionizes by a chemical process such as an acid treatment or an alkaline treatment. More specifically, examples of the ionized functional group encompass: a carboxyl group, a dicarboxyl group, dithiocarbamic acid ion, amine, ethylene diamine, pyridine, and the like.

The functional group may also be a non-ionized functional group (neutral functional group) or the like, for example, which is bondable with the calcium phosphate sinter itself by coordination bonding.

(Substrate)

A substrate of a percutaneous terminal used in the present invention is preferably elastic. Materials such as a medical plastic, an elastomer and the like are suitably used for materials to form the substrate. Examples of the medical plastic and the elastomer encompass: a fluororesin (fluorine-included resin) such as polytetrafluoroethylene, a silicone resin such as silicone rubber, vinyl chloride resin, vinylidene chloride resin, fluoridated silicone rubber, polyethylene, polypropylene, polycarbonate, polyester, polyhydroxyethyl (metha) acrylate, polyacrylamide, polysulfone, polyether sulfone, poly-N-vinylpyrrolidone, segmented polyurethane, and the like. The material to form the substrate is preferably the same material as the medical tubing to be inserted to the attained percutaneous terminal. In order to have a good bio-affinitive ceramics composite coating, the substrate may be surface processed by for example, etching, glow discharging process, application of coupling agent, or other processes.

The following describes the shape of the substrate, however the shape is not limited to this. For example, the substrate can be of a tubular shape. Inside the tubular shape, the medical tubing is to be inserted.

The substrate preferably has a flange section. The following describes a percutaneous terminal which has the flange section.

The substrate according to the present embodiment has a body section 101 and a flange section 102, as illustrated in FIGS. 5 through 10. A plurality of the flange section 102 may be provided. A medical tubing is to be inserted in the inside (inner side) of the body section 101. The body section 101 and the flange section 102 may be formed by using the same material, or may be formed by using different material. The substrate may be arranged such that a hole section 103 is provided on the flange section 102. In such arrangement, a plurality of the hole sections 103 may be provided. The following description deals with this arrangement.

The body section 101 fixes the percutaneous terminal 100 to the medical tubing. The body section 101 is shaped extending in an inserting direction of the medical tubing to be inserted in the body section 101. The body section 101 is tubular-shaped; a shape of a plane perpendicular to the inserting direction of the medical tube (cross sectional shape) is a circle or an oval. The length of the body section 101 in the medical tubing inserting direction differs depending on the purpose of use. For example, if the percutaneous terminal is used for a catheter for pulmonary hypertension treatment (central venous catheter to be placed in the body for a long term), a sufficient length is around 0.5 mm to 2 cm, and if the percutaneous terminal is used for a catheter for peritoneal dialysis, the sufficient length is around 0.5 mm to 4 cm. An inside diameter of the body section 101 is around the same measurement as a girth of the medical tubing to be inserted in the percutaneous terminal 100. A thickness (radial thickness) of the body section 101 differs depending on the purpose of use. Provided that the radial thickness of the medical tubing to be inserted to the percutaneous terminal 100 is 100%, the thickness of the body section 101 is more preferably in a range of more than 0 to 10000%, and is further preferable in a range of 100 to 5000%. The percutaneous terminal 100 is appropriately fixed to the medical tubing by having the thickness of the body section 101 within the aforementioned range.

The flange section 102 suppresses movement and rotation of the substrate (percutaneous terminal 100) with respect to the extending direction of the medical tubing. The medical tubing connects the outside of the living body to the inside of the living body when implanted to the living body. The medical tubing mainly receives external force in the extending direction of the medical tubing. The movement of the percutaneous terminal 100 in the extending direction of the medical tubing (inserting direction of the percutaneous terminal to the medical tubing) is suppressed even when the force is received, by providing a flange section 102 on the percutaneous terminal 100.

It is known that a contortion due to the external force and the movement of the living body causes the medical tubing to receive a rolling force in a rotating direction of the cylinder of the medical tubing. By thus providing the flange section 102 to the percutaneous terminal 100, the movement of the percutaneous terminal 100 in the rotating direction of the medical tubing (rotating direction of the medical tubing around the body of the percutaneous terminal) is suppressed.

The flange section 102 may be provided around the whole or a part of the girth of the body section 101. A plurality of the flange section 102 may be provided to the body section 101. More specifically, for example, the flange section 102 may be provided on both ends of the body section 101, or on one end of the body section 101. In addition, the flange section 102 is provided so that the area of the flange section 102 is larger than the area of the body section 101, when the flange section 102 is seen from the inserting direction of the medical tubing of the percutaneous terminal 100, in other words the axis direction of the percutaneous terminal.

The flange section 102 may be provided around the whole or a part of the girth of the body section 101. A plurality of the flange section 102 may be provided to the body section 101. More specifically, for example, the flange section 102 may be provided on both ends of the body section 101, or on one end of the body section 101. The flange section 102 may also be provided in the mid part of the body section 101. In addition, the flange section 102 is provided so that the area of the flange section 102 is larger than the area of the body section 101, when the flange section 102 is seen from the inserting direction of the medical tubing of the percutaneous terminal 100, in other words the axis direction of the percutaneous terminal.

In addition, the flange section 102 is arranged projecting from the body section 101 in a predetermined angle with respect to the axis direction of the body section 101 (axis direction of the percutaneous terminal 100). More specifically, the flange section 102 preferably projects from the body section 101 in the angle in a range of 30° to 150°, when the flange section 102 is seen from the axis direction of the body section 101. By thus providing the flange 102 slanted in a predetermined angle with respect to the axis direction of the body section 101, the catheter fixed to the percutaneous terminal 100 can be placed along the living body for example when the percutaneous terminal 100 is implanted inside the living body. The slanting angle of the flange section 102 with respect to the axis direction of the body section 101 differs depending of the purpose. For example, if the percutaneous terminal 100 is to fix a central venous catheter, the angle is preferably in a range of 10° to 170°, and further preferable in a range of 20° to 160°. Of the above slanting angles, considering from the viewpoint of bio-affinity of the percutaneous terminal attained at the end, the slanting angle is particularly preferred in a range of 60° to 120°. In a viewpoint such that the percutaneous terminal is used by implanting the percutaneous terminal inside the living body, the slanting angle is particularly preferred in a range of 15° to 45° (135° to 165°).

The following description deals with the preferable shape of the percutaneous terminal 100 in order to fix the central venous catheter to be placed in the body for a long term. When implanting the central venous catheter to be placed in the body for a long term in the living body, specifically, the catheter is to be implanted from around the chest, and so that the catheter extends to the outside of the living body. It is possible to extend the catheter to the outside of the living body along the living body by providing the flange 102 of the percutaneous terminal 100 on the body section 101 in the predetermined angle as above.

It is preferable for an area of the flange section 102 when seen from the inserting direction of the medical tubing, in other words, the area of the flange section 102 in the cross section perpendicular to the axis direction of the body section 101, to be in a range of more than 0 to up to 10, and is further preferable in a range of 0.05 to 5. Note that the area of which the cross section surface perpendicular to the axis direction of the body section 101 and the area of a centrum inside the body section 101 are added together is calculated as 1.

Figure 5:
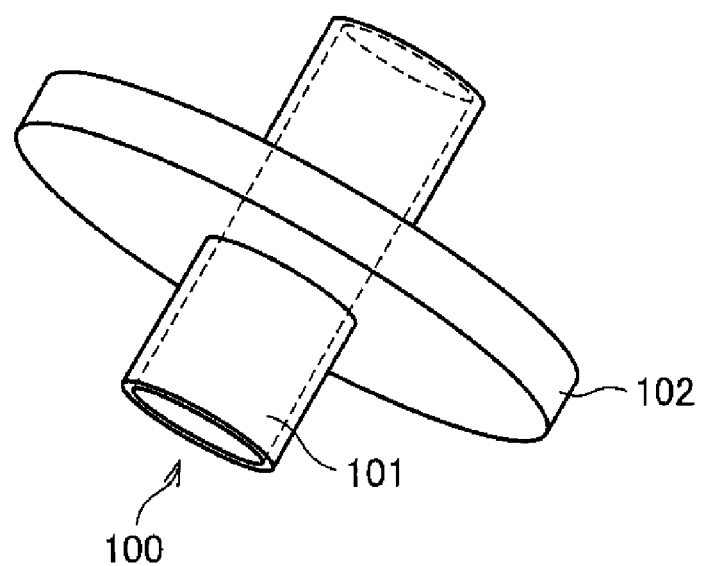
FIG. 5 is a perspective view illustrating a shape of a substrate constructing a percutaneous terminal (one example).
Figure 6:
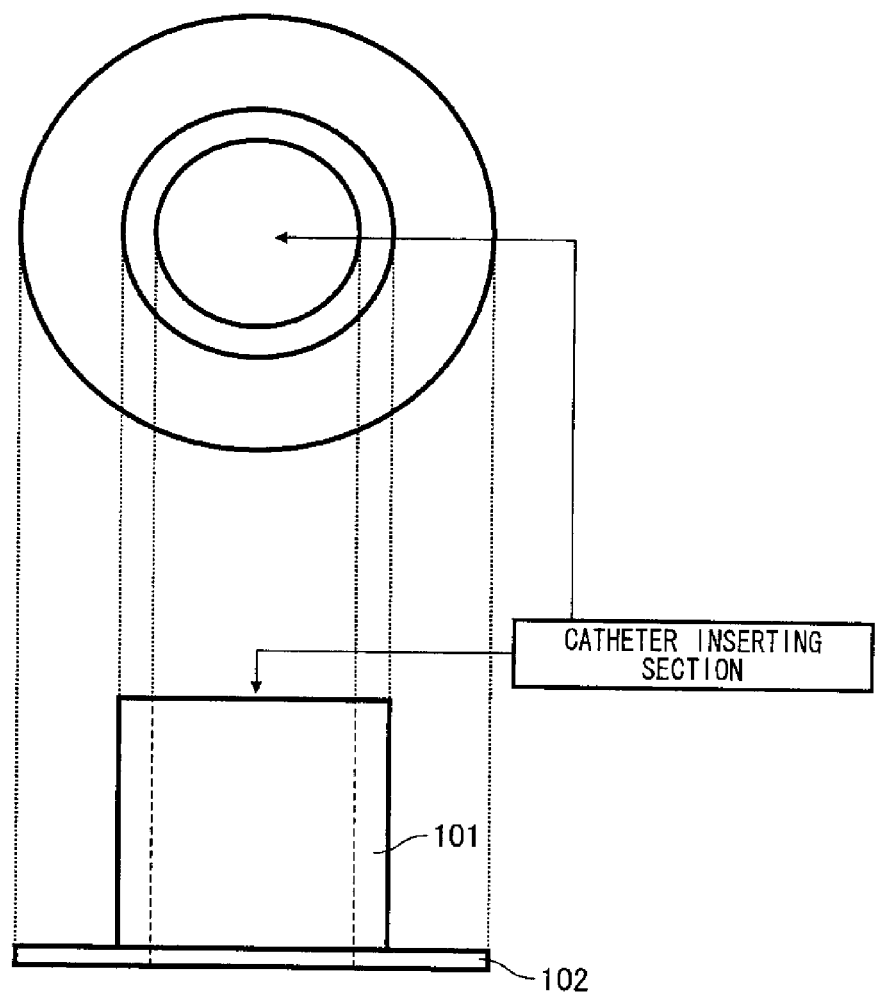
FIG. 6 is a top view and a front view illustrating another shape of a substrate constructing a percutaneous terminal (one example).
Figure 7:
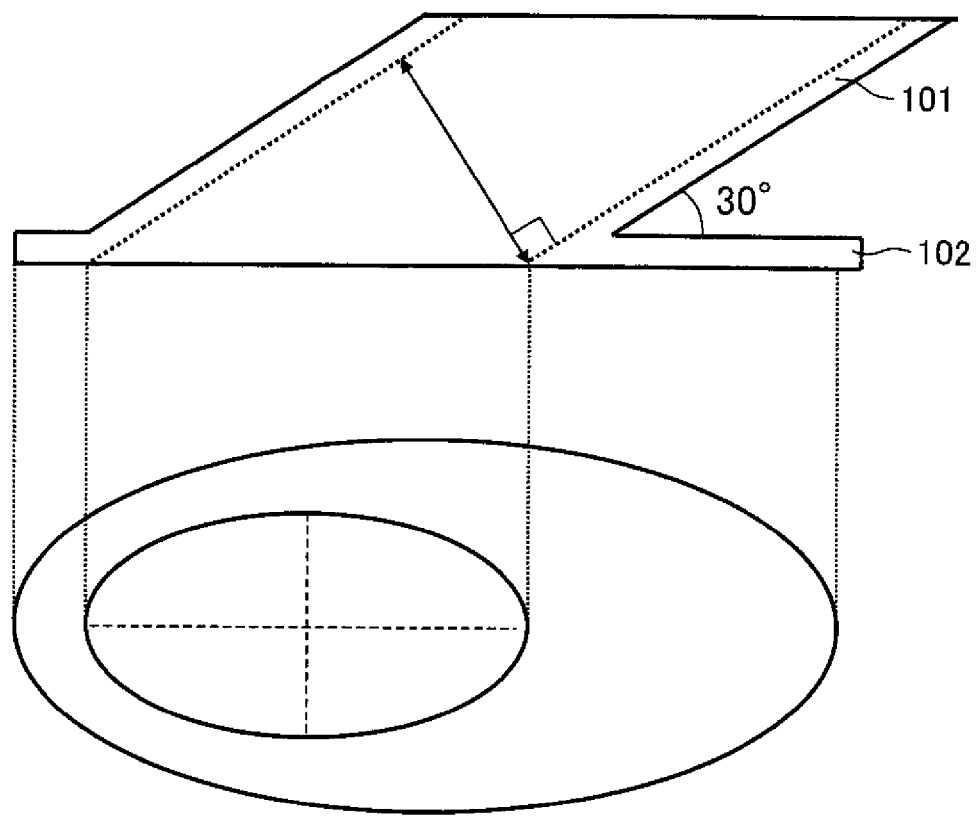
FIG. 7 is a top view and a front view illustrating yet another shape of a substrate constructing a percutaneous terminal (one example).
Figure 8:
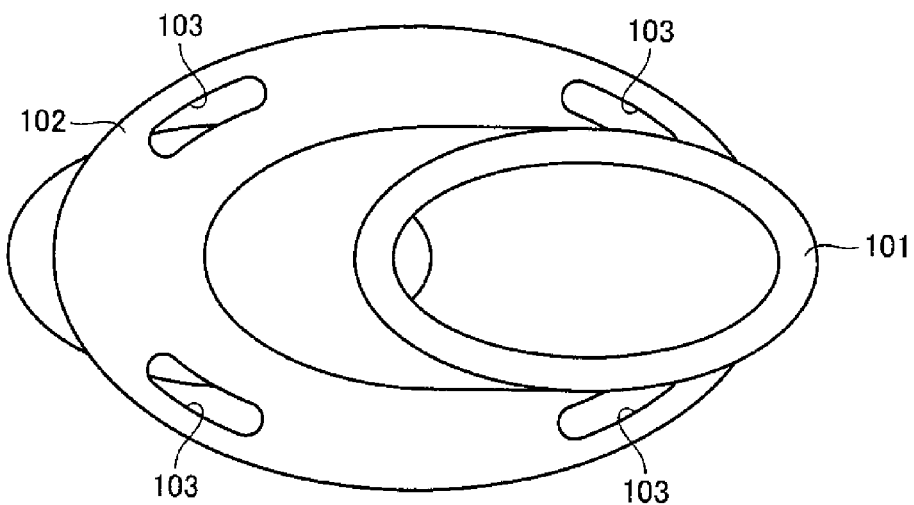
FIG. 8(a) is a top view schematically illustrating a percutaneous terminal where a hole section is formed on a flange section.
FIG. 8(b) is a side view schematically illustrating a percutaneous terminal where a hole section is formed on a flange section.
Figure 8:
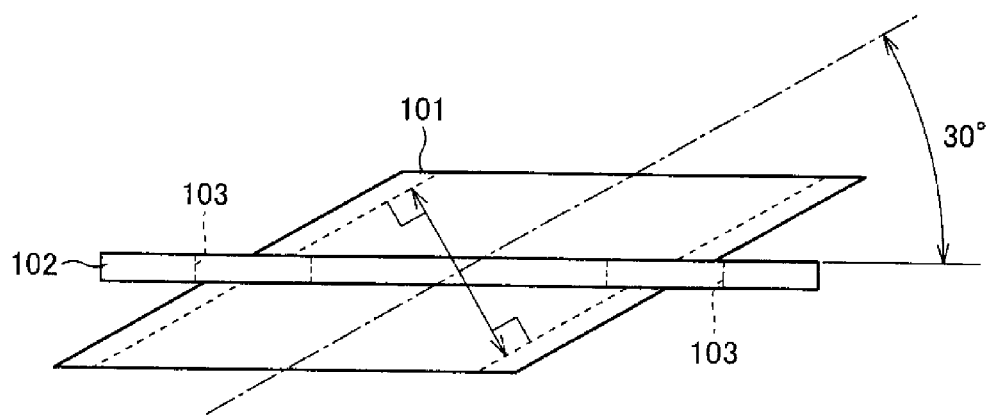
Figure 9:
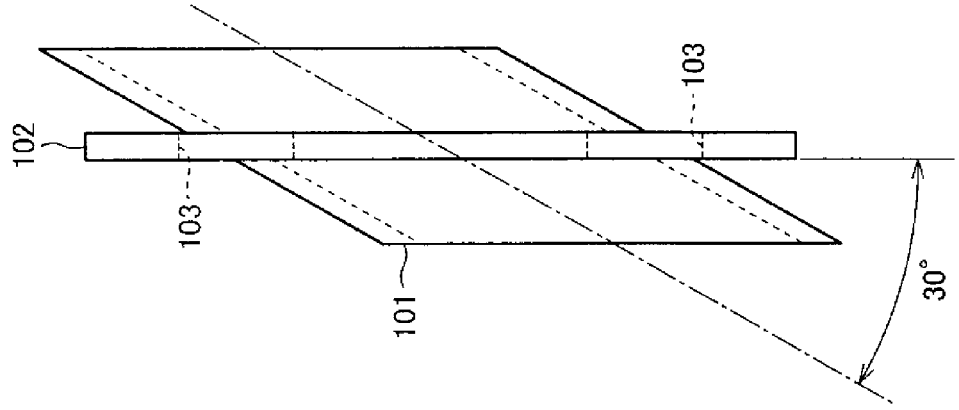
FIG. 9(a) is a top view schematically illustrating a giant flying squirrel type percutaneous terminal.
FIG. 9(b) is a side view schematically illustrating a giant flying squirrel type percutaneous terminal.
Figure 9:
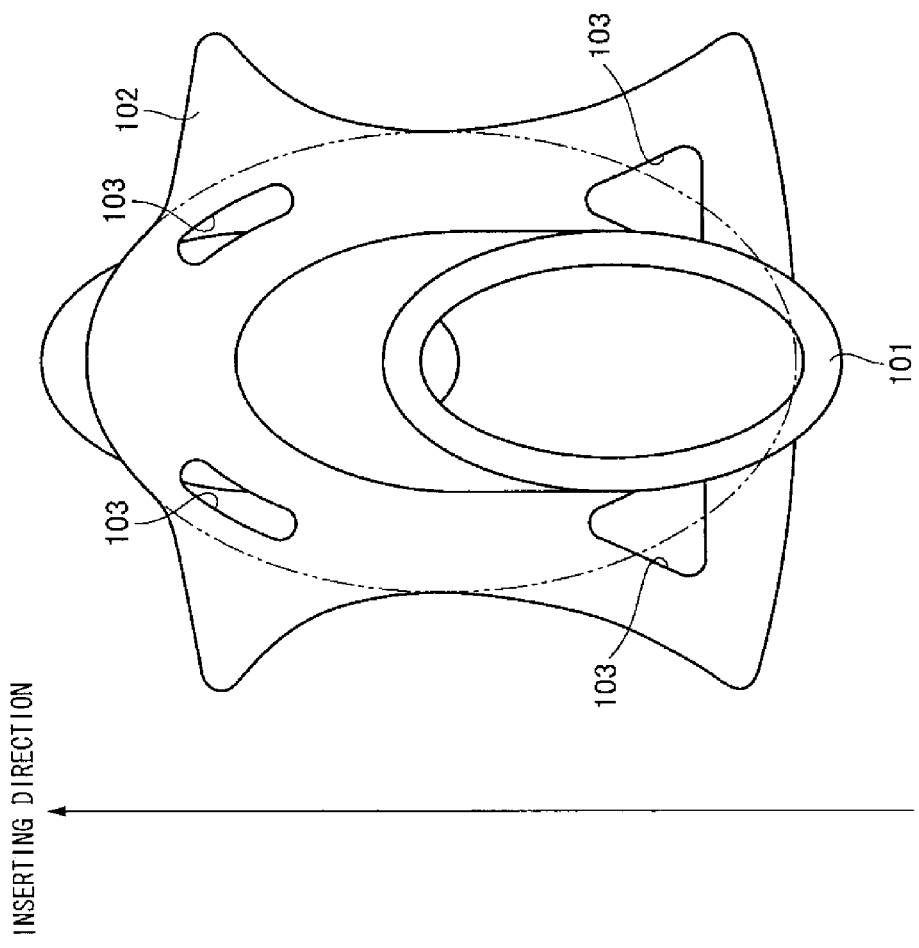
Figure 10:
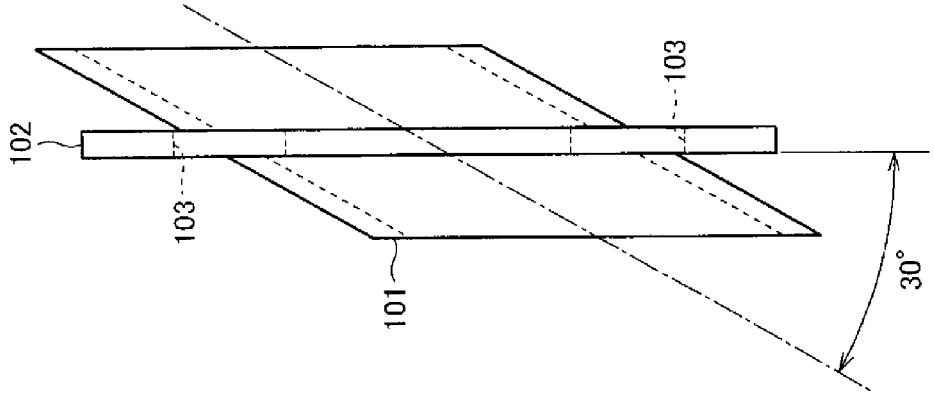
FIG. 10(a) is a top view schematically illustrating a space shuttle type percutaneous terminal.
FIG. 10(b) is a side view schematically illustrating a space shuttle type percutaneous terminal.
Figure 10:
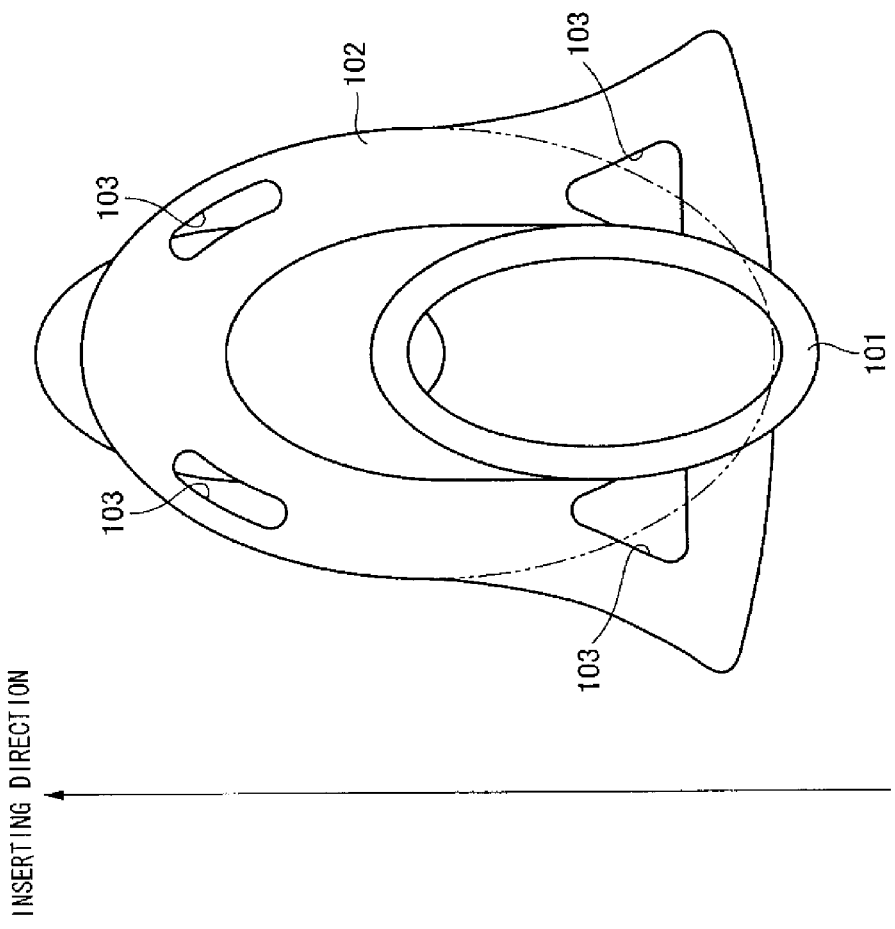

Namely, the shape of the substrate may be one where the flange section 102 is provided around the mid part of the body section 101 along the axis direction of the substrate as illustrated in FIG. 5. The shape of the substrate may be one where the flange section 102 is provided on the end of the body section 101 as illustrated in FIG. 6. The shape of the substrate further may be arranged where the flange section 102 is provided in a predetermined angle with respect to the axis direction of the substrate, as illustrated in FIG. 7. In addition, for example, the flange section 102 may be provided on both ends of the body section 101, and these flange sections 102 may project to just one part of a surrounding of the body section 101. Furthermore, the flange section 102 provided on both ends of the body section 101 may be provided in a predetermined angle with respect to the axis direction of the substrate.

The shape of the flange section 102 is required to be of a shape which can accomplish the easiness of implanting in the living body and the high adhesiveness with the living body, when implanting the flange section 102 to the living body. More specifically, the percutaneous terminal 100 has a percutaneous terminal inner side surface and a percutaneous terminal outer side surface with respect to the extending direction of the medical tubing. Thus, the easiness of implantation may differ for the percutaneous terminal 100 depending on the flange section 102, more specifically, the symmetry of the flange section 102. The explanation of this is dealt with in the following description.

The implantation of the medical tubing and the percutaneous terminal 100 is performed in the following method: (i) a part of an epithelium of the implanting part of the living body is incised; (ii) the medical tubing is punctured and indwelled; and (iii) the medical tubing is inserted into the living body. The flange section 102 of the percutaneous terminal on an inner side surface of percutaneous terminal 100 is preferably shaped having a narrow tip so that the medical tubing is easily inserted (implanted) to the living body when puncturing the medical tubing to the living body. In addition, the flange section 102 is preferably broad in area in order to have a broad adhering surface with the living body.

From these two viewpoints, the flange section of the percutaneous terminal 100 is preferably shaped such that the flange section 102 has, on the inserting side, a tapered shape with a narrow a tip, so that it is easy to insert the medical tubing in the living body when inserting the medical tubing. The flange section 102 on the opposite side with respect to the inserting side is preferably projected, so that the side has a broader area (broader adhering surface with respect to the living body).

More specifically, the shapes as illustrated in FIGS. 9(a), 9(b), 10(a) and 10(b) are preferable.

The flange section 102 as illustrated in FIGS. 9(a) and 9(b) is shaped as if a giant flying squirrel is opening its membrane in order to attain buoyant force from air. The inner side surface of the percutaneous terminal 100 is seen as the direction of the head of the giant flying squirrel. In detail, the percutaneous terminal 100 illustrated in FIGS. 9(a) and 9(b) is of a shape in which four parts of the flange section 102 are further projecting, and tips of the flange section 102 in the inserting side is shaped thinner than the other parts in order for the percutaneous terminal 100 to be inserted to the living body.

The flange section 102 illustrated in FIGS. 10(a) and 10(b) is shaped as though a space shuttle is broadening its wings in order to attain buoyant force from air. The inner side surface of the percutaneous terminal 100 is seen as the flying direction of the space shuttle. In details, the percutaneous terminal 100 illustrated in FIGS. 10(a) and 10(b) is in a shape where two parts of the flange section on the rear side of the percutaneous terminal 100 are projecting. The rear side denotes the rear side of the percutaneous terminal in an implanting direction when implanted to the living body.

This arrangement enables easy insertion (implantation), and improves the adhesiveness with the biological tissues. Furthermore, by thus improving the adhesiveness, the movement and the rotation of the percutaneous terminal 100 with respect to the inserting direction of the medical tubing is suppressed.

The flange section 102 of the percutaneous terminal 100 is preferably arranged such that a plurality of hole sections 103 is provided. The following description deals with the explanation of this.

FIGS. 8(a) and 8(b) are drawings schematically illustrating an arrangement of the percutaneous terminal 100 in which the hole sections 103 are provided on the flange section 102. The hole sections 103 are provided to suppress the movement of the substrate with respect to the extending direction, and the rotation movement of the medical tubing. The medical tubing connects the outside of the living body and the inside of the living body, when the medical tube is implanted inside the living body. The medical tubing mainly receives external force in an extending direction of the medical tubing. By thus providing the hole sections 103 on the flange section 102 of the percutaneous terminal 100, the movement of the percutaneous terminal 100 in the extending direction of the medical tubing (inserting direction of the percutaneous terminal 100 of the medical tubing) is suppressed. It is also known that the medical tubing receives rolling force, due to the contortion of the medical tubing caused by the external force received and the movement of the living body. This causes the medical tubing to rotate. By providing the hole sections 103 on the flange section 102 of the percutaneous terminal 100, the movement and the rotation of the percutaneous terminal 100 in a rotating direction of the medical tubing (rotating direction of the girth of the percutaneous terminal 100 of the medical tubing) is suppressed.

More specifically, the existence of the hole sections 103 on the flange section 102 enables the biological tissues existing inside the living body to extend and pass through the hole sections 103 of the percutaneous terminal 100 when the percutaneous terminal 100 is implanted inside the living body. Consequently, the biological tissues adhering on the surface of the flange section 102 and the extended tissues adhere with each other. The percutaneous terminal 100 is thus sewn onto the living body, as though tissues work as a thread to sew on the flange section 102 through the hole sections 103. This thus fixes the percutaneous terminal 100 on the living body. The fixing of the percutaneous terminal 100 suppresses the movement and the rotation of the percutaneous terminal 100 with respect to the inserting direction of the medical tubing. That is to say, by providing holes on the flange section 102 of the percutaneous terminal 100, the tissues on each side of the flange section 102 adhere with each other via the hole sections 103. This attains the fixing of the percutaneous terminal 100 in the living body, and thus suppresses the rotation of the percutaneous terminal 100.

The hole sections 103 may be provided on just one part of the flange section 102, or may be provided on the whole area of the flange section 102. Furthermore, the hole sections 103 may be provided in plurals. More specifically, the hole section 103 may be provided in the center part of the flange section 102 (middle of flange) for example, or may be provide on the end part of the flange section 102. A plurality of hole sections 103 do not require to be arranged symmetrical with respect to the shape of the flange section 102.

The number of hole sections 103 arranged on the flange section is preferably in a range of 1 to 20, more preferably in a range of 2 to 10, and particularly preferable in a range of 4 to 8.

The movement and the rotation of the percutaneous terminal with respect to the extending direction of the medical tubing is further suppressed by providing the hole sections 103 on the flange section 102 as the aforementioned.

If the number of the hole sections 103 is too many (if more than 20 hole sections are provided, for example 30 hole sections 103) the area of the flange section 102 becomes small. This causes insufficient mechanical properties of the percutaneous terminal 100. If the number of hole sections 103 is too many, the size of the hole sections 103 arranged on the flange section 102 becomes comparatively small. This may cause insufficient attainment in suppression effect of the movement with respect to the extending direction of the medical tubing and rotation of the medical tubing, due to insufficient passing through of the biological tissues via the hole sections 103.

The plurality of hole sections 103 provided on the flange section 102 is more preferably arranged in symmetry with respect to a line perpendicular to an extending axis (extending direction) of the body section 101. By thus arranging the plurality of the hole sections 103 in symmetry, the movement and the rotation of the percutaneous terminal 100 are adequately suppressed.

The total area of all the hole sections 103 arranged on the flange section 102 is preferably in a range of more than 0 to 40%, more preferably in a range of 0.1 to 30%, and particularly preferably in a range of 1 to 20%, each with respect to the area of the flange section 102 seen from the inserting direction of the medical tubing. Note that the area of the flange section 102 is 100%, and this area includes the area of the hole sections arranged on the flange section. However, the area of the cross section plane of the body section 101 perpendicular to an axis direction, of which the cross section is on the same plane, is not included.

If the total area of the hole sections 103 is larger than 40%, the proportion of the hole sections 103 with respect to the flange section 102 is too large. This causes insufficient mechanical properties of the percutaneous terminal 100 itself. Additionally, the area of each hole section 103 is large in this case, therefore enough force to fix the percutaneous terminal 100 may not be attained, even if the tissues which pass through the hole sections 103 adhere with the other biological tissues. As a result, the suppression effect of the movement and the rotation of the percutaneous terminal 100 with respect to the extending direction of the medical tubing may not be sufficiently attained.

The hole sections 103 arranged on the flange section 102 may be, for example, circle-shaped, oval-shaped, triangular-shaped, quadrilateral-shaped, or even an indeterminate shape.

Furthermore, all of the hole sections 103 arranged on the flange section 102 do not require to be the same shape, and the plurality of hole sections 103 may be of different shapes.

(Percutaneous Terminal)

A percutaneous terminal according to the present invention is one which a surface of a substrate of the percutaneous terminal is flocked with bio-affinitive short fibers. The percutaneous terminal may be produced by, for example, a method according to the present invention, and by an apparatus according to the present invention, each of which are later described.

The surface of the substrate of the percutaneous terminal according to the present invention is flocked with bio-affinitive short fibers, whereby a major axis of the short fibers is risen perpendicular to (or substantially perpendicular to) the surface of the percutaneous terminal. Therefore, the surface area of the percutaneous terminal is significantly larger compared to a conventional percutaneous terminal. The conventional percutaneous terminal has the major axis of the bio-affinitive short fiber adhered on the surface of the percutaneous terminal parallel (or substantially parallel) to the surface of the percutaneous terminal, or the surface of the percutaneous terminal is coated with a bio-affinitive material. The larger surface area indicates that the area of the bio-affinitive material which has contact with the biological tissues is larger. As a result, the adhesiveness of the percutaneous terminal with the biological tissues is improved.

Figure 4:
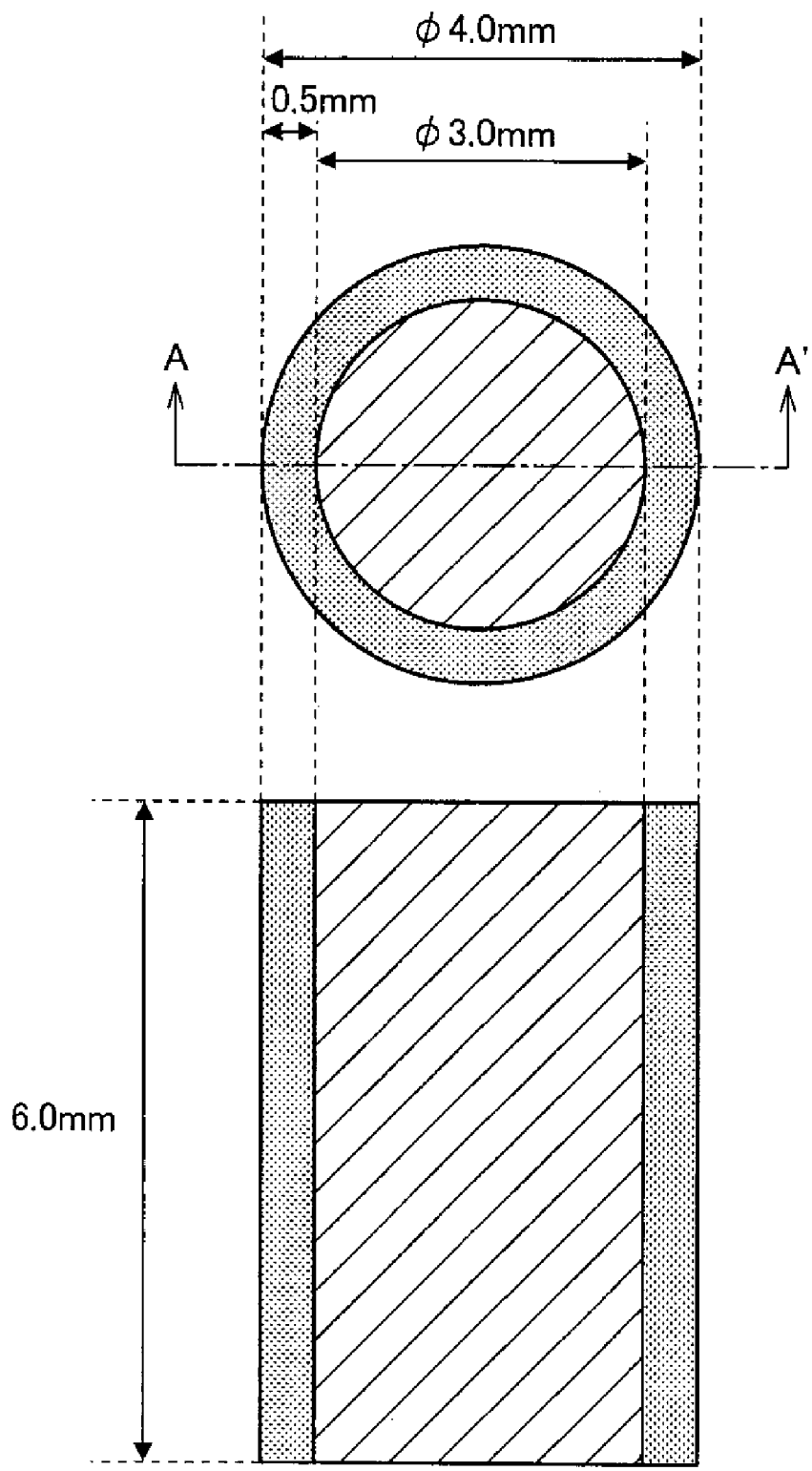
FIG. 4 is a top view and a cross sectional view taken on line A-A', of a T1 type percutaneous terminal ($\phi$=4.0 mm, height=6.0 mm) created by coating a bio-affinitive material on a surface of a substrate of a cylindrical percutaneous terminal ($\phi$=3.0 mm, height=6.0 mm) so that the thickness of the coating is 0.5 mm.

The following describes a comparison result of the surface areas using a diagram, comparing the area of the surface of the substrate of the percutaneous terminal when the surface of the substrate of the percutaneous terminal is (i) flocked with bio-affinitive short fibers, or (ii) coated with the bio-affinitive material, without the flocking process. FIG. 4 illustrates a top view of a T1 type percutaneous terminal ($\phi$=4.0 mm, height=6.0 mm), and a cross sectional view taken on line A-A'. The T1 type percutaneous terminal is produced so that on a surface of a substrate of a cylindrical percutaneous terminal ($\phi$=3.0 mm, height=6.0 mm), a bio-affinitive material is coated with a thickness of 0.5 mm. A medical tubing is to be inserted inside the cylinder (shown in drawing with a diagonal line). When the percutaneous terminal is implanted inside the living body, the outside surface of the cylinder is in contact with the biological tissues. Therefore, the area of the bio-affinitive material of the T1 type percutaneous terminal which has contact with the biological tissues will be:

$$2 \times \pi \times 2.0 \text{ mm} \times 6 \text{ mm} = 75.40 \text{ mm}^2$$

In comparison, the area of the percutaneous terminal of which the surface of the substrate thereof is flocked with the bio-affinitive short fibers is as follows. Assume that cylindrical short fibers of a diameter of 10 μm and a height of 100 μm are adhered one each in a standing state per matrix form of 20 μm each of the surface of the substrate of the percutaneous terminal ($\phi$=3.0 mm, height=6.0 mm). The surface area (excluding the adhering surface with the substrate of the percutaneous terminal) of the fiber in an average 100 μm (diameter=10 μm) is:

$$(0.01\pi \times 0.1) + (0.005 \times 0.005)\pi,$$

and the number of short fibers adhered on the surface of the substrate of the percutaneous terminal is:

$$(3 \text{ mm} \times \pi \times 6 \text{ mm}) \div (0.02 \text{ mm} \times 0.02 \text{ mm}).$$

Therefore, the area of the surface of which the bio-affinitive short fibers have contact with the biological tissues is as follows:

$$((0.01\pi \times 0.1) + (0.005 \times 0.005)\pi) \times (3 \text{ mm} \times \pi \times 6 \text{ mm}) \div (0.02 \text{ mm} \times 0.02 \text{ mm}) = 482.78 \text{ mm}^2$$

Consequently, the area of the surface of which the bio-affinitive material has contact with the biological tissues in the case where the bio-affinitive short fibers are flocked on the surface of the substrate of the percutaneous terminal is approximately 6.4 times larger, compared to the percutaneous terminal of which the bio-affinitive material is coated on the substrate of thereof without the flocking process. As such, it is clear that the former percutaneous terminal is higher in bio-adhesiveness compared to the latter percutaneous terminal.

The area of which the bio-affinitive material has contact with the biological tissues broadens by flocking the bio-affinitive short fibers on the surface of the substrate coated with the bio-affinitive material. Therefore, such aspect is also within the scope of the present invention.

The percutaneous terminal according to the present invention is preferably arranged such that the surface area of the short fibers which coat the unit area of the substrate of the percutaneous terminal to the unit area of the substrate of the percutaneous terminal is at least twice more, more preferably 3 times or more, and most preferred as 4 times or more. The aforementioned values are calculated, for example, in the following process: (i) the number of short fibers implanted in the unit area of the surface of the substrate of the percutaneous terminal (for example 1 mm$^2$) is found by a scan-type electron microscope; (ii) a surface area of the short fibers (excluding the adhering surface with the substrate) is found; (iii) a surface area of the short fibers which coat the unit surface of the substrate of the percutaneous terminal is calculated from the number of short fibers and the surface area of the short fiber (excluding the adhering surface with the substrate); and (iv) the calculated amount is compared with the unit area. It is preferred to calculate the value for two or more places on the percutaneous terminal, and to find the average, in order to attain a more accurate value in the proportion of the unit area of the substrate of the percutaneous terminal and the surface area of the short fibers which coat the unit area.

The following description deals with a use example of the percutaneous terminal of the present invention. The percutaneous terminal according to the present invention may have various medical tubings inserted thereto. Specific purposes of the percutaneous terminal which are suitable are, for example, a catheter for treatment of pulmonary hypertension (central venous catheter to be placed in the body for a long term), a catheter for peritoneal dialysis, skin insertion section of an artificial vessel of a ventricular assist device (VAS) for sending or removing blood, an artificial anus/bladder, a catheter for high calorie, a gastric fistula, a percutaneous electrode, an external shunt, and blood access.

[2. Method and Apparatus According to the Present Invention for Producing the Percutaneous Terminal]

A method according to the present invention for producing the percutaneous terminal is a method for producing a percutaneous terminal in which a surface of a substrate of the percutaneous terminal is flocked with bio-affinitive short fibers, the method including the steps of: arranging, between a first electrode plate and a second electrode plate, the substrate of the percutaneous terminal in which an adhesive is applied on the surface thereof; mounting the bio-affinitive short fiber on the second electrode plate; rotating the substrate of the percutaneous terminal; and applying a voltage to the first electrode plate and the second electrode plate, the first electrode plate and the substrate of the percutaneous terminal being electrically connected. In the step of arranging, between a first electrode plate and a second electrode plate, the substrate of the percutaneous terminal in which an adhesive is applied on the surface thereof, the substrate of the percutaneous terminal is preferably arranged between the first electrode plate and the second electrode plate in such that the first electrode plate and the second electrode plate make an angle or angles in a range of more than 0° to less than 90° with respect to an inserting direction in which a medical tubing is to be inserted to the percutaneous terminal. The method according to the present invention is preferably a method which further includes a step of moistening the bio-affinitive short fibers, in addition to the aforementioned arrangement.

An apparatus according to the present invention for producing the percutaneous terminal is an apparatus for producing a percutaneous terminal in which a surface of a substrate of the percutaneous terminal is flocked with bio-affinitive short fibers, the apparatus including: a first electrode plate and a second electrode plate; and a rotation supporting section which includes a supporting section for supporting the substrate of the percutaneous terminal and a rotation section for rotating the supporting section, the second electrode plate being arranged under the first electrode plate where a direction of gravity is denoted as downwards; the second electrode plate being arranged such that the bio-affinitive short fibers are mountable; the rotation supporting section being arranged so that the substrate of the percutaneous terminal, which substrate is supported by the supporting section is to be arranged between the first electrode plate and the second electrode plate; and the supporting section being electrically connected with the first electrode plate, and arranged electrically connectable with the substrate of the percutaneous substrate. In addition, the rotation supporting section in the apparatus of the present invention may be arranged such that the substrate of the percutaneous terminal, which substrate is supported by the supporting section is arranged between the first electrode plate and the second electrode plate, so that the first electrode plate and the second electrode plate make an angle or angles in a range of more than 0° however less than 90° with respect to an inserting direction in which a medical tubing is to be inserted to the percutaneous terminal.

The method according to the present invention for producing the percutaneous terminal is suitably performed by, for example, the aforementioned apparatus according to the present invention for producing the percutaneous terminal. The following description deals with the method and apparatus according to the present invention for producing the percutaneous terminal, by using one example of the apparatus according to the present invention for producing the percutaneous terminal. However, the present invention is not limited to this.

Figure 3:
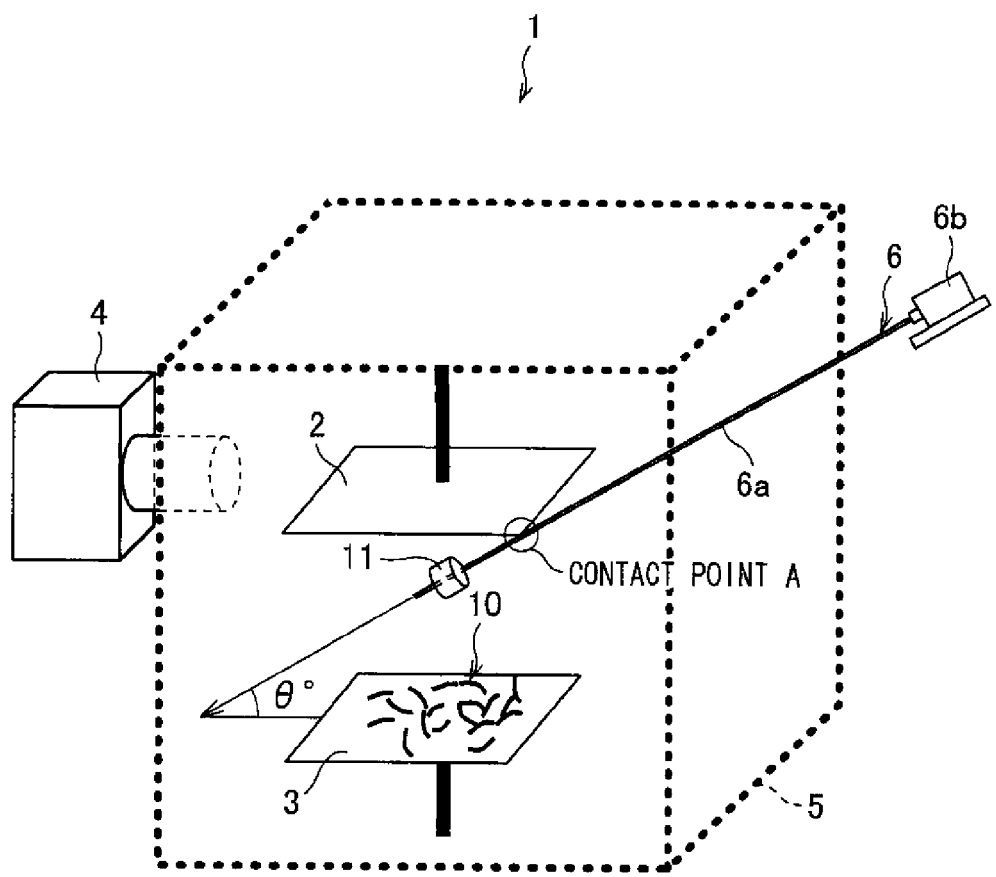
FIG. 3 is a schematic diagram illustrating one embodiment of an apparatus according to the present invention.

FIG. 3 illustrates a schematic diagram of one embodiment of an apparatus (flocking device 1) for producing the percutaneous terminal according to the present invention. The pertaining flocking device 1 includes a first electrode plate 2, a second electrode plate 3, a rotation supporting section 6 which includes a supporting section 6a and a rotating section 6b, a temperature controlling section 4 which includes a humidity sensor and a humidifier, and a container 5.

The first electrode plate 2 and the second electrode plate 3 in the flocking device 1 are arranged substantially parallel to each other, and the first electrode plate 2 is arranged on top of the second electrode plate 3, in the condition that the direction of gravity is denoted as low. The first electrode plate 2 and the second electrode plate 3 are tabular electrodes. The two electrode plates are electrically connected to a power source (not illustrated), so that a voltage is applicable between the two electrode plates. Short fibers 10 are mounted on the second electrode plate 3.

In the flocking device 1, the supporting section 6a of the rotation supporting section 6 is bar-shaped, and the substrate 11 of the percutaneous terminal is supported by the bar-shaped supporting section 6a. The method for supporting the substrate 11 of the percutaneous terminal by the supporting section 6a is not particularly limited, and may be, for example, supported by inserting the bar-shaped supporting section 6a in the medical tubing inserting section of the substrate 11 of the percutaneous terminal as like in FIG. 3, or a tip of the supporting section 6a may be made in a shape of a clamp, and may support the substrate 11 of the percutaneous terminal by sandwiching the percutaneous terminal with the clamp. The supporting section 6a is a bar-shape in FIG. 3, however the apparatus according to the present invention is not limited to the bar-shape. Even if the supporting section 6a is of a bar-shape, it is not limited to a straight-form, and may be curved or sharply bent.

The rotation supporting section 6 is arranged so that the substrate 11 of the percutaneous terminal supported by the supporting section 6a is arranged between the first electrode plate 2 and the second electrode 3 in an angle more than 0° however less than 90° with respect to the first electrode plate 2 and the second electrode plate 3 in the inserting direction in which the medical tubing is to be inserted to the percutaneous terminal. The angle denotes an angle between a straight line parallel to the inserting direction in which the medical tubing is to be inserted to the percutaneous terminal and the plane surface of the first electrode plate and the second electrode plate. The angle particularly indicates a narrow angle (acute angle) of the angles formed by the straight line and the plane surface. In FIG. 3, the angle is indicated as "θ°". In the apparatus of the present invention, the angle is more than 0° however less than 90°. In case the short fibers 10 are flocked on the surface of the substrate 11 of a percutaneous terminal of a complex shape as like a percutaneous terminal provided with a body section and a flange section, one of the body section and the flange section is often not facing the flying direction of the short fibers 10, in the following cases: (i) the angle is 0°, that is, the inserting direction of the medical tubing to the percutaneous terminal is parallel to the plane surface of the first electrode plate 2 and the second electrode plate 3; or (ii) the angle is 90°, that is, the inserting direction of the medical tubing to the percutaneous terminal is perpendicular to the plane surface of the first electrode plate 2 and the second electrode plate 3. Therefore, it is difficult to evenly flock the short fibers 10 on the surface of the substrate 11 of the percutaneous terminal. Although the angle is not particularly limited provided that the angle is more than 0° however less than 90°, it is further preferred to be in a range of more than 5° to less than 85°, and most preferred in a range of more than 10° to less than 80°.

In the apparatus according to the present invention for performing the percutaneous terminal, the supporting section 6a is electrically connected to the first electrode plate 2, and is arranged electrically connectable with the substrate 11 of the percutaneous terminal. That is to say, the first electrode plate 2 and the substrate 11 of the percutaneous terminal are electrically connected. By the electrical connection of the first electrode plate 2 and the substrate 11 of the percutaneous terminal, electromotive force generates on the bio-affinitive short fibers 10. This rises the bio-affinitive short fibers 10. In order to arrange the apparatus as the above, the supporting section 6a requires to be at least conductive. As such, it is preferable for the supporting section 6a to be made of a conductor. The conductor is not particularly limited, and may be a metal such as Cu, Fe, Ni, Pt or the like, or a material such as carbon or a conductive polymer. The method of electrically connecting the supporting section 6a and the first electrode plate 2 is not particularly limited. For example, the supporting section 6a and the first electrode plate 2 may partially have contact with each other as illustrated by a contact point A in FIG. 3.

The supporting section 6a is connected to the rotating section 6b. The supporting section 6a and the substrate 11 of the percutaneous terminal supported by the supporting section 6a thus rotates. The rotating section 6b in the flocking device 11 is constructed by an electric motor. However, the rotating section 6b is not particularly limited, provided that the rotating section 6b is a mean which can rotate the supporting section 6a. That is to say, the supporting section 6a may be constructed by the electric motor, or may be constructed by an engine. Furthermore, the rotating section 6b is arranged as a bearing of the supporting section 6a, and may be arranged so that the supporting section 6a is rotated by manpower. A rotation rate is not particularly limited, however, for example, the rotation rate is preferably in a range of not less than 0.1 to less than 1000 rpm, further preferably in a range of not less than 0.5 to less than 500 rpm, and most preferred in a range of not less than 1 to less than 100 rpm. If the rotation rate exceeds the preferable range, a centrifugal force received by the substrate 11 of the percutaneous terminal becomes too heavy. This causes peeling off of the adhesive on the substrate 11 of the percutaneous terminal, or deformation in shape. If the rotation rate is under the preferable range, the adhesive runs down, and causes non-uniformity in adhering.

The flocking device 1 includes a container 5, and a humidity controlling section 4 which includes a humidity sensor and a humidifier. The container 5 contains the first electrode 2, the second electrode 3, and the supporting section 6a. The humidity sensor and a part of the humidifier, each in the humidity controlling section, are inserted to the container 5, and controls the humidity inside the container. The short fibers 10 mounted on the second electrode plate 3 are kept at a suitable humidity for flocking, by thus controlling the humidity inside the container. The most suitable humidity is as previously mentioned. A conventional, publicly known mean is to be appropriately selected and adopted for the humidity controlling section 4.

The shape of the container 5 is not particularly limited, however, the container 5 is preferably arranged so that one part of the container 5 can be opened. In other words, the container is preferred to have a door structure which can open and close. Such arrangement enables to easily set the short fibers 10 and the substrate 11 of the percutaneous terminal to the container, to easily collect the produced percutaneous terminals, and to easily clean the inside of the container 5. It is also preferable for the container 5 to be one which can be made sealed or semi-sealed in order to thoroughly control the humidity inside the container 5.

The flocking device 1 may include, other than the aforementioned arrangement, a breaker for preventing an electrical leak, a process notification lamp for notifying that the flocking is in process, a door opening and shutting switch for indicating the opening or shutting of the container 5, a buzzer and a lamp for indicating abnormality of process, and other components.

The following description explains one example of a method for producing the percutaneous terminal, by using the flocking device 11.

(i) The substrate 11 of the percutaneous terminal in which an adhesive is applied on the surface thereof is fixed to the supporting section 6b of the rotation supporting section 6. Publicly known adhesives are adoptable as appropriate for the adhesive. Examples of these encompass: a silicone adhesive; a polyethylene-vinyl acetate copolymer; polyester; nylon; urethane elastomer; vinyl acetate; acrylic resin; and the like.

(ii) The bio-affinitive short fibers 10 are mounted on the second electrode plate 4. The bio-affinitive short fibers described in the section "1. Percutaneous terminal of the present invention" are used as appropriate for the short fibers 10.

(iii) Shut the lid of the container 5.

(iv) Operate the humidity controlling section 4.

(v) Rotate the substrate 11 of the percutaneous terminal by operating the rotating section 6b of the rotation supporting section 6.

(vi) Apply a voltage to the first electrode plate 2 and the second electrode plate 3. The applied voltage is adapted by considering the most appropriate voltage depending on the distance between the electrodes, the size, material and the like of the short fibers 10, and the material of the supporting section 6a. Usually, the voltage is preferably in a range of 1 to less than 100 kV, further preferably in a range of 2 to less than 75 kV, and most preferable in a range of 5 to less than 50 kV.

The order of the steps (i) and (ii) is transposable. The step of (iv) may be performed anywhere before or after the steps of (i), (ii), (iii), (v) or (vi). The step of (v) may be performed at any timing, provided that the step (v) is performed after the step of (i).

By performing the above operations, the percutaneous terminal in which the short fibers 10 are flocked on the surface of the substrate 11 thereof is produced.

The method according to the present invention for producing the percutaneous terminal is not limited to the above steps, and may further include a step applying an adhesive, a step drying the percutaneous terminal which has been subject to flocking, a step removing unnecessary short fibers from the surface of the percutaneous terminal electrically adhered to the percutaneous terminal, and other steps. In addition, each of the aforementioned steps may be altered in order as appropriate in the scope that the method according to the present invention for producing the percutaneous terminal is performed.

[3. Medical Instrument to be Placed in the Body According to the Present Invention]

A medical instrument to be placed in the body according to the present invention is one which has a substrate whose surface is flocked with bio-affinitive short fibers.

The following description deals with one embodiment of the medical instrument to be placed in the body according to the present invention. The explanation in the section [1. Percutaneous terminal according to the present invention] can be cited for the case where the percutaneous terminal according to the present invention is the medical instrument to be placed in the body according to the present invention. This section will describe the differences to the section of [1. Percutaneous terminal according to the present invention]. That is to say, the arrangement not described in this section apply correspondingly to the description in the section of [1. Percutaneous terminal according to the present invention].

The "medical instrument to be placed in the body" in the present specification denotes a medical instrument to be used placed inside the living body. The "medical instrument" in the present specification denotes the "medical instrument" as defined in the Pharmaceutical Affairs Law of Japan, in Item 4 of Section 2. More specifically, the "medical instrument" denotes the medical instrument listed in the attached table of Section 1 in the Pharmaceutical Affairs Law enforcement example of Japan.

That is to say, the medical instrument to be flocked with the bio-affinitive short fibers is not limited, provided that the medical instrument is one to be used placed inside the living body, and is the medical instrument stipulated in the Pharmaceutical Affairs Law. However, it is preferable for the medical instrument to be selected from the group consisting of an artificial vessel, a stent, a stent graft, an artificial trachea, a pace maker, an artificial heart, and an access port. These medical instruments particularly require suppression of disposition inside the living body. The medical instrument to be placed in the body on which the surface of the substrate is flocked with the bio-affinitive short fibers enable to suppress the disposition of the medical instrument, because of the excellent adhesiveness with the biological tissues.

The percutaneous terminal according to the present invention preferably includes a flange section. In comparison, the medical instrument to be placed in the body according to the present invention may be arranged such that the flange section is provided as necessary, depending on the type of the medical instrument to be placed in the body.

The medical instrument to be placed in the body according to the present invention not only includes the medical instruments which connect the inside of the body to the outside of the body, but also includes the medical instruments which implant the whole instrument inside the body, for example an artificial heart. The medical instruments that are implanted by the whole have a further problem of disposition inside the body when compared with the medical instrument which connects the inside and the outside of the body. However, the medical instrument to be placed in the body is also suitable for medical instruments which are implanted inside the body by the whole, due to the high adhesiveness with the living body, and the secure position stability.

[4. Method and Apparatus According to the Present Invention for Producing the Medical Instrument to be Placed in the Body]

A method according to the present invention for producing the medical instrument to be placed in the body is a method for producing a medical instrument to be placed in the body in which a surface of a substrate of the medical instrument to be placed in the body is flocked with bio-affinitive short fibers, the method including the steps of: arranging, between a first electrode plate and a second electrode plate, the substrate of the medical instrument to be placed in the body in which an adhesive is applied on the surface thereof; mounting the bio-affinitive short fibers on the second electrode plate; rotating the substrate of the medical instrument to be placed in the body; and applying a voltage to the first electrode plate and the second electrode plate, the first electrode plate and the substrate of the medical instrument to be placed in the body being electrically connected. In addition, the method according to the present invention is preferably a method further including the step of moistening the bio-affinitive short fibers.

An apparatus according to the invention for producing the medical instrument to be placed in the body is an apparatus for producing a medical instrument to be placed in the body in which a surface of a substrate of the percutaneous terminal is flocked with bio-affinitive short fibers, the apparatus including: a first electrode plate and a second electrode plate; and a rotation supporting section which includes a supporting section for supporting the substrate of the percutaneous terminal and a rotating section for rotating the supporting section, the second electrode plate being arranged under the first electrode plate, where a direction of gravity is denoted as downwards, the second electrode plate being arranged such that the bio-affinitive short fibers are mountable, the rotation supporting section being arranged so that the substrate of the medical instrument to be placed in the body, which substrate is supported by the supporting section is to be arranged between the first electrode plate and the second electrode plate, the supporting section being electrically connected with the first electrode plate, and arranged electrically connectable with the substrate of the percutaneous substrate.

The method according to the present invention for producing the medical instrument to be placed in the body is suitably performed by, for example, the apparatus according to the present invention for producing the medical instrument to be placed in the body.

The description in the aforementioned section [2. Method and apparatus according to the present invention for producing the percutaneous terminal] can be cited for the case the method and the apparatus according to the present invention for producing the percutaneous terminal is the method and the apparatus according to the present invention for producing the medical instrument to be placed in the body. That is to say, the specific arrangement of the method and the apparatus according to the present invention for producing the medical instrument to be placed in the body apply correspondingly to the description in the section of [2. Method and apparatus according to the present invention for producing the percutaneous terminal].

In the method and apparatus according to the present invention for producing the percutaneous terminal, the substrate of the percutaneous terminal in which the adhesive is applied on the surface thereof is preferably arranged between the first electrode and the second electrode, so that the first electrode and the second electrode make an angle or angles of more than 0° however less than 90° with respect to the inserting direction in which the medical tubing is to be inserted to the percutaneous terminal, in the step of arranging the substrate of the percutaneous terminal in which the adhesive is applied to the surface thereof. The method and apparatus according to the present invention for producing the medical instrument to be placed in the body is not limited to this. That is to say, the angle of the arrangement between the first electrode and the second electrode may be set as appropriate, depending on the type and form of the medical instrument to be placed in the body.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

In addition, all of the professional documents and the Patent Documents mentioned in the present description are cited as reference in the present description.

EXAMPLE

The following description deals with the present invention in detail by using an example. However, the present invention is not limited to the examples and comparative examples.

Production Example 1 is shown as follows, which produces a hydroxyapatite composite particle used as the short fibers in Example 1 and Comparative Example 1.

Production Example 1

Production Method for Hydroxyapatite Sinter

The following description deals with the production method for the hydroxyapatite sinter according to the present example.

A continuous oil layer of 40 ml including 0.5 g of a non-ionic detergent is prepared, by using dodecane as the continuous oil phase and pentaethylene glycol dodecyl ether whose cloudy sky atmosphere is 31° C. as the non-ionic detergent. Then, 10 ml of a Ca(OH)$_2$ dispersing aqueous solution (2.5 mol %) is added to the prepared continuous oil layer. Next, after sufficiently stirring the fluid dispersion, 10 ml of KH$_2$PO$_4$ solution of 1.5% mol is added to the water/oil (W/O) emulsion, and was made to react in a reacting temperature of 50° for 24 hours. During the reaction, the solution was stirred. By thus separating the obtained reactants by centrifugation, hydroxyapatite is obtained. The hydroxyapatite is heated for one hour in the temperature of 800° C., which produced a hydroxyapatite sinter particle (hereafter referred as HAp particle). The HAp particle is of a single crystal form, and the long diameter is in a range of 300 to 400 nm.

(Production Method of a Hydroxyapatite Composite Particle)

Firstly, a fiber-shaped silk fibroin (manufactured by Fujimura Seishi, product name: Habutae, hereafter referred as SF fiber) is cut so that an average length in a major axis direction is 100 μm, and the average length in a minor axis direction is 10 μm. Extraction and removal of fixed components from the obtained SF fiber (hereafter referred as cutSF) was performed by a Soxhlet extractor.

Following this, 600 mg of the cutSF which has been subject to the Soxhlet extraction is placed inside a doctor test tube. 82 mg of ammonium peroxodisulfate melted in 18 ml of pure water is added to this cutSF. In addition, a solution adding and sufficiently stirring 292 μl of pentaethylene glycol dodecyl ether to 1088 μl of γ-methacryloxy propyltrimetoxy silane (KBE503) is also added to the doctor test tube. This mixture was then frozen, degassed, thawed, and substituted by liquid nitrogen, and then repeated the same process of freezing, degassing, thawing and substituting, once more.

The reacting solution was reacted by heating the solution for 60 minutes by a water-bath of a temperature of 50° C. Following this, the reacting solution was filtered by using a qualitative filter paper (retaining particle diameter=5 μm). This separated the silk fibroin fibers (filter cake) on which an alkoxysilyl group is introduced on the surface of the cutSF, and molecules (filtrate) of which a polymerized KBE and a silyl group are esterified. Additionally, in order to separate the polymerized KBE, the silk fibroin fibers which introduce the alkoxysilyl group on the surface of the cutSF were sonicated (output of 20 kHz, 35 W) for one minute in ethanol. The silk fibroin fibers were further washed by stirring the ethanol for two hours, were filtered with the qualitative filter paper, and vacuum dried. Thus, the silk fibroin fibers is obtained, in which the end of the silk fibroin fiber is graft polymerized with a polymer chain containing the alkoxysilyl group. In other words, an alkoxysilyl group introduced silk fibroin fiber (hereafter referred as KBE-cutSF) is obtained. The introduction rate of the alkoxysilyl group in the reaction time was 8.3% by weight. The introduction rate was calculated by the following formula. Note that the weight of the unprocessed cutSF is A g, and the weight of the cutSF which has completed the reaction (KBE-cutSF) is B g.

Introduction rate (% by weight)=$((B-A)/A)\times 100$

On the other hand, 300 mg of the HAp particles was added to 15 ml of a solvent (toluene:methanol=8.6:1), and dispersed by sonication for 20 seconds. After the sonication has completed, the mixture was left standing for 30 minutes to one hour.

While the HAp particles were left standing, approximately 300 mg of the KBE-cutSF was dispersed in 15 ml of a solvent (toluene:methanol=8.6:1), in an Erlenmayer of 30 ml.

A supernate solvent of which the HAp particles were dispersed was quietly transferred to the Erlenmayer in which the KBE-cutSF was dispersed, by using a Pasteur pipette. Following this, the dispersion solvent which has the KBE-cutSF and the HAp particles combined were quietly stirred with the pipette once every minute.

After repeating the stirring operation ten times, the KBE-cutSF of which the HAp particles were absorbed (hereafter referred as "KBE-cutSF-HAp") and the unabsorbed HAp particles were separated by the qualitative filter paper. More specifically, the supernatant HAp particles were filtered, and then the precipitated KBE-cutSF-HAp was collected.

The separated KBE-cutSF-HAp was stirred and washed in ethanol for two hours, sonicated for one minute, and filtered with the qualitative filter paper.

The filtered KBE-cutSF-HA was dried in 60° C., and processed for two hours in a temperature of 120° C., in 1 mmHg. This thus elaborates the hydroxyapatite composite particle (KBE-cutSF-HAp). It was found that the HAp particles were bonded to the base material, as a result of analyzing the elaborated hydroxyapatite composite particles by using an FT-IR (diffused reflection method).

Example 1

The following description deals with a method for producing a percutaneous terminal by flocking the substrate with the KBE-cutSF-HAp.

The flocking device 1 as illustrated in FIG. 3 was used for the production of the percutaneous terminal. The steps were taken following the description of the section [2. Method and apparatus according to the present invention]. The conditions of the flocking were as follows:

| | |
|---|---|
| Power source voltage | direct current (DC): 25 kV |
| Distance between first electrode plate and second electrode plate | approximately 50 mm |
| Distance between second electrode plate and substrate of percutaneous terminal | approximately 15 mm |
| Distance between second electrode plate and substrate of percutaneous terminal | approximately 35 mm |

-continued

| Humidity control | relative humidity of 95% |
| Rotation rate of rotation supporting section | 3 rpm |
| Processing time | 5 minutes |
| Temperature inside apparatus | 25° C. |
| Use of an atomizer | Yes |

The KBE-cutSF-HAp was moistened with the atomizer before the KBE-cutSF-HAp was processed.

In addition, application of an adhesive to the substrate was processed as the same as the following [Comparative Example 1].

Comparative Example 1

The following description deals with the method for producing the percutaneous terminal by coating the KBE-cutSF-HAp on the substrate.

Firstly, a cover tape was winded around the surface of the substrate on where the KBE-cutSF-HAp is not covered (parts except for the coating section).

Next, a silicone adhesive (manufactured by GE Toshiba Silicone Co., Ltd., noncorrosive quick-drying adhesive sealing material, TSE-399) was applied to the substrate, while the substrate was rotated with an axis in the inserting direction of the catheter in the silicon rubber substrate in a rotation rate of 360 rpm. The substrate was next rotated in a rotation rate of 5600 rpm for 10 seconds to remove excess adhesive.

The KBE-cutSF-HAp was evenly applied to the substrate on which the adhesive is applied, while the substrate was rotated in the rotation rate of 360 rpm. Following this, excess KBE-cutSF-HAp was removed.

Following this, the substrate coated with the KBE-cutSF-HAp was dried for five minutes in a temperature of 85° C., and was taken off the rotating bar five minutes later. This was then dried for two hours in a vacuum atmosphere (133 Pa (1 mmHg)) of 120° C.

Next, the substrate is soaked in pure water, and is washed by radiating ultrasonic waves (output of 20 kHz, 35 W) for three minutes. After the completion of the ultrasonic wave radiation, the substrate is further washed by stirring the substrate in the pure water for one hour. The substrate was dried, and left standing for 24 hours. Thus, the percutaneous terminal according to the present invention is produced. Note that the cover tape is removed after the KBE-cutSF-HAp was adhered to the substrate on which the adhesive was applied.

Figure 2:
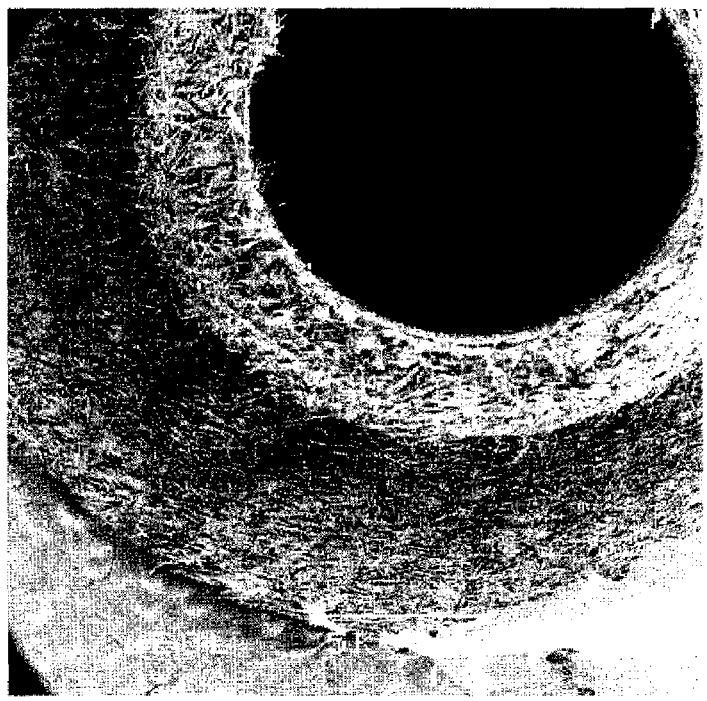
FIG. 2(a) is a scanning electronography of a percutaneous terminal produced in Comparative Example 1.
FIG. 2(b) is a scanning electronography of a percutaneous terminal produced in Comparative Example 1.
Figure 2:
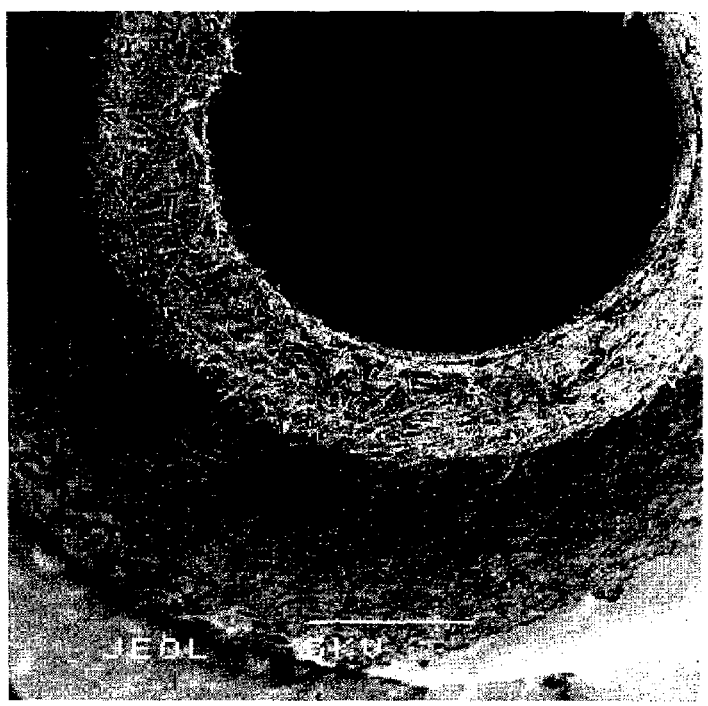

FIG. 1 illustrates a scanning electronography of the percutaneous terminal produced in Example 1. FIGS. 2(a) and 2(b) illustrate a scanning electronography of the percutaneous terminal produced in Comparative Example 1. It can be seen that the fibers of the KBE-cutSF-HAp are adhered on the surface of the percutaneous terminal in a lying state in FIGS. 2(a) and 2(b). In comparison, the percutaneous terminal illustrated in FIG. 1 has the fibers of the KBE-cutSF-HAp adhered on the surface of the percutaneous terminal in a rising state. Therefore, the percutaneous terminal pertaining to Example 1 obviously has a broader surface area compared to the percutaneous terminal pertaining to Comparative Example 1.

Example 2

Evaluation of Flocking Density

The present Example performed an evaluation of flocking density of the percutaneous terminal produced by the operations and conditions described in Example 1.

The evaluation of the flocking density was performed by cutting off one part of the flocked percutaneous terminal, and observing the surface of the part with a scanning electron microscope (SEM) (manufactured by Japan Electro Optical Laboratory Ltd. (JEOL Ltd.)). More specifically, the magnification was set as 100-power, and the number of flock existing within a square of a length of a side as 200 µm was counted. Five squares were randomly picked out for counting the number of flock, and the average value of the number of flock was evaluated as the flocking density.

The same operations were taken for the percutaneous terminal produced by the operations and conditions described in Comparative Example 1, and the flocking density thereof was evaluated.

A result of comparing (i) the flocking density of the percutaneous terminal produced by the operations and conditions described in Example 1 and (ii) the flocking density of the percutaneous terminal produced by the operations and conditions described in Comparative Example 2, are as shown in Table 1.

TABLE 1

| | Example 1 | Comparative Example 1 |
|---|---|---|
| Flocking density | 20 ± 2 strands/40,000 µm² (18-22 strands/40,000 µm²) | 5 ± 4 strands/40,000 µm² (1-9 strands/40,000 µm²) |

It was shown that it is possible to flock the KBE-cutSF-HAp with a higher flocking density than the conventional technique, by flocking the percutaneous terminal.

Example 3

Controlling the Flocking Density

The present Example produced the percutaneous terminal in the method and condition described in Example 1 and evaluated the flocking density in the method described in Example 2, however the power source voltage and the relative humidity were changed. The specific conditions of the power source voltage and the relative humidity, and the flocking density of the percutaneous terminal attained from these conditions are shown in Table 2.

TABLE 2

| Power source voltage | 10 kV | 25 kV | 30 kV |
|---|---|---|---|
| Relative humidity | 60% | 95% | 95% |
| Flocking density (strand/40,000 µm²) | 5 ± 1 (4-6) | 20 ± 2 (18-22) | 27 ± 4 (23-31) |

As shown in Table 2, it was demonstrated that it is possible to control the flocking density of the percutaneous terminal by adjusting the power source voltage and the relative humidity. The flocking density was uncontrollable in the method and the conditions described in Comparative Example 1.

Example 4

Flocking on a Stent

Figure 11:
FIG. 11 is a view illustrating an external view of a stent (one example) which has not been subjected to flocking.

The following description deals with a method for flocking a substrate of a 316L Palmaz-Schatz stent made of stainless steel (hereafter referred as simply "stent" in the present example) with the KBE-cutSF-HAp. FIG. 11 is a view illustrating an external view of the stent which has not been subjected to flocking.

The flocking device 1 illustrated in FIG. 3 was used for the production of the stent, and the steps were taken according to the explanation in the section [2. Method and Apparatus according to the present invention]. The conditions of the flocking were as follows:

| | |
|---|---|
| Power source voltage | direct current (DC): 25 kV |
| Distance between first electrode plate and second electrode plate | approximately 50 mm |
| Distance between second electrode plate and substrate of stent | approximately 15 mm |
| Distance between substrate of stent and first electrode plate | approximately 35 mm |
| Humidity control | relative humidity of 95% |
| Rotation rate of rotation supporting section | 3 rpm |
| Processing time | 5 minutes |
| Temperature inside apparatus | 25° C. |
| Use of an atomizer | Yes |

The same adhesive described in Comparative Example 1 was used for the adhesive. The object was to flock just the surface of the stent, therefore the adhesive was applied by lightly pressing an absorbent cotton soaked with the adhesive against the substrate of the stent.

Figure 12:
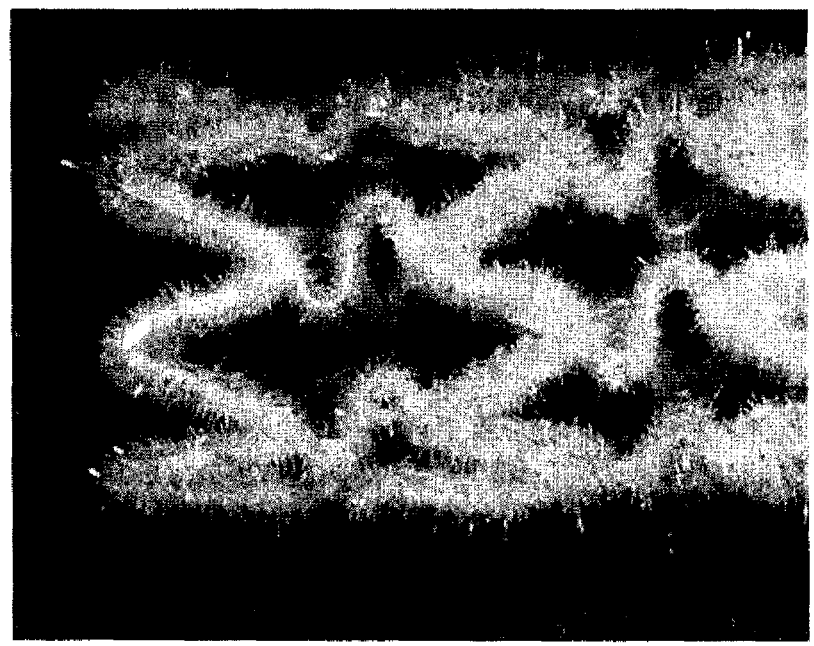
FIG. 12 is a view illustrating an external view of a stent (one example) which has been subjected to flocking.

FIG. 12 illustrates the flocked stent. It was demonstrated, as illustrated in FIG. 12, that the KBE-cutSF-HAp adhered on the surface of the stent in a three-dimensional rising state.

Example 5

Flocking on a Graft

Artificial Vessel

The following description deals with a method for flocking the KBE-cutSF-HAp on a substrate of a graft made of a synthetic polymer material (Dacron) (hereafter referred as simply "graft" in the present example).

The graft was obtained in a method described in the Japanese Patent Application No. 2005-203517. The flocking device 1 illustrated in FIG. 3 was used for the flocking on the graft, and the steps were taken according to the explanation in the section of [2. Method and apparatus according to the present invention]. The conditions of the flocking and the application method of the adhesive were performed in the operations and conditions described in Example 3.

As a result, it was demonstrated that the KBE-cutSF-HAp adhered on the surface of the graft in a three-dimensional rising state.

Example 6

Animal Testing

The present Example studied on how a catheter affected a rabbit when the following catheters were implanted in the rabbit's body: (i) a percutaneous-terminal-mounted catheter, which mounts the percutaneous terminal produced in the operations and conditions described in Example 1; (ii) a cuffed catheter (manufactured by C. R. Bard, product name: Hickman Catheter, specification: single-lumen, standard: 9.6 FR, length: 90 cm, inside diameter: 1.6 mm), which mounts a cuff made of Dacron (polyester fiber); and (iii) a silicone made catheter (hereafter referred as "control catheter") used in Example 1, in which the percutaneous terminal is not mounted.

The method described in Japanese Unexamined Patent Publication, Tokukai, No. 2005-342508, of "Animal Implanting Experiment" was used for implanting the catheters to the rabbits. More specifically, the experiment was conducted in the following steps.

First, each of the catheters was sterilized by an autoclave.

Next, a rabbit (Japanese White) was incised at a cervical (back side) epidermis thereof, and a subepidermic percutaneous tunnel was created. The catheter was inserted to the produced percutaneous tunnel. For implanting the percutaneous terminal mounted catheter, the percutaneous terminal was fixed in a position straight below the cervical incision section, and the incision section was sutured. For implanting the cuffed catheter also, the cuff was fixed in a position straight below the cervical incision section, and the incision section was sutured. As such, one catheter was implanted per rabbit. 10 rabbits were implanted the percutaneous terminal mounted catheter, 10 rabbits were implanted the cuffed catheter, and 10 rabbits were implanted the control catheter.

The catheter implanted rabbits were observed twice a day, and the natural evulsions of the catheter was assessed. In addition, the occurrence and generation of inflammation and tumor were determined. If there were any abnormalities, the implanted catheters were evulsed. Note that the stitches were removed from the sutured section 14 days later from the day the catheter was implanted. The observation continued for 84 days, and the number of remaining rabbits of which the catheter was implanted was counted. The result of this is shown in Table 3 and FIG. 13.

TABLE 3

| | | 4 weeks later | 8 weeks later | 12 weeks later |
|---|---|---|---|---|
| Percutaneous terminal mounted catheter | Number remaining | 9 | 8 | 7 |
| | Number which generated tumor | — | — | — |
| Cuffed catheter | Number remaining | 9 | 6 | 5 |
| | Number which generated tumor | 1 | — | 1 |
| Control catheter | Number remaining | 4 | 4 | None survived |
| | Number which generated tumor | 1 | 1 | — |

Figure 13:
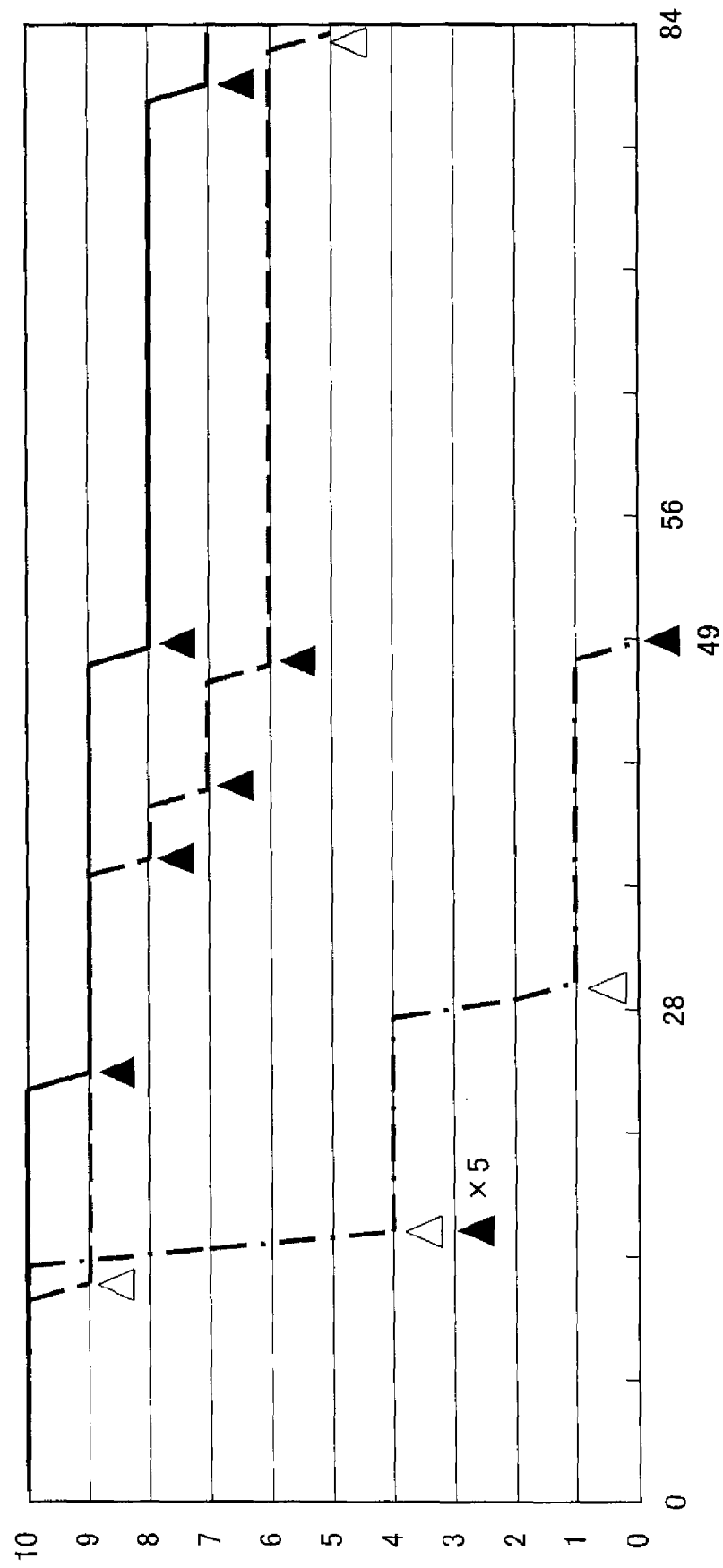
FIG. 13 is a view illustrating a result of the counted remaining number of rabbits which has a catheter implanted therein.

FIG. 13 shows the result of the number of remaining rabbits which had a catheter implanted therein. The vertical axis is the remaining number of rabbits, and the horizontal axis shows the number of days of which has past since the implantation. The solid line, the broken line, and the one-dot chain line indicate the remaining number of rabbits which have the percutaneous terminal mounted catheter, the cuffed catheter, and the control catheter implanted, respectively. The black triangles in FIG. 13 indicate the natural evulsions of the catheter, and the white triangles indicate that the catheter was evulsed due to determination of tumor or the like. The black triangle with the "×5" indicates that the natural evulsions of the catheter occurred in five rabbits at that point.

As shown in Table 3 and FIG. 13, the percutaneous terminal mounted catheter according to the present invention, compared to the cuffed catheter and the control catheter, has a high adhesiveness with the living body and suppresses disposition. Furthermore, the result shows that the percutaneous terminal mounted catheter suppresses bacterial infection.

Industrial Applicability

The percutaneous terminal according to the present invention is suitable for a percutaneous terminal fixing a medical catheter implanted for a long term inside a living body. Thus, the present invention is useful particularly in the medical field and the medical instruments field. The medical instrument to be placed in the body according to the present invention is excellent in adhesiveness with the biological tissues, thereby prevents the displacement inside the living body. Moreover, the medical instrument of the present invention enables the prevention of the infection of bacteria. Thus, the medical instrument to be placed in the body of the present invention is useful for medical instruments implanted in the body, for example, artificial vessels, stents, artificial tracheas, pace makers, artificial hearts, access ports, and the like.

The invention claimed is:

1. An apparatus for producing a percutaneous terminal in which a surface of a substrate of the percutaneous terminal is flocked with bio-affinitive short fibers, the apparatus comprising:
   a first electrode plate and a second electrode plate; and
   a rotation supporting section which includes a supporting section for supporting the substrate of the percutaneous terminal and a rotating section for rotating the supporting section, the second electrode plate being arranged under the first electrode plate, where a direction of gravity is denoted as downwards;
   the second electrode plate being arranged such that the bio-affinitive short fibers are mountable;
   the rotation supporting section being arranged so that the substrate of the percutaneous terminal, which substrate is supported by the supporting section is to be arranged between the first electrode plate and the second electrode plate; and
   the supporting section being electrically connected with the first electrode plate, and arranged electrically connectable with the substrate of the percutaneous substrate, the supporting section being a bar, an angle formed by a longitudinal direction of the supporting section and each of the first electrode plate and the second electrode plate being more than 0° however less than 90°.

2. The apparatus as set forth in claim 1, further comprising moistening means for moistening the bio-affinitive short fibers.

3. The apparatus as set forth in claim 1, further comprising:
   a container for containing at least the first electrode plate, the second electrode plate and the supporting section; and
   a humidity controlling section for controlling humidity inside the container.

4. An apparatus for producing a medical instrument to be placed in the body in which a surface of a substrate of the medical instrument to be placed in the body is flocked with bio-affinitive short fibers, the apparatus comprising:
   a first electrode plate and a second electrode plate; and
   a rotation supporting section which includes a supporting section for supporting the substrate of the medical instrument to be placed in the body and a rotating section for rotating the supporting section,
   the second electrode plate being arranged under the first electrode plate, where a direction of gravity is denoted as downwards, the second electrode plate being arranged such that the bio-affinitive short fibers are mountable,
   the rotation supporting section being arranged so that the substrate of the medical instrument to be placed in the body, which substrate is supported by the supporting section is to be arranged between the first electrode plate and the second electrode plate,
   the supporting section being electrically connected with the first electrode plate, and arranged electrically connectable with the substrate of the percutaneous substrate, the supporting section being a bar, an angle formed by a longitudinal direction of the supporting section and each of the first electrode plate and the second electrode plate being more than 0° however less than 90°.

5. The apparatus as set forth in claim 4, further comprising humidifying means for humidifying the bio-affinitive short fibers.

6. The apparatus as set forth in claim 4
   a container for containing at least the first electrode plate, the second electrode plate and the supporting section; and
   a humidity controlling section for controlling a humidity inside the container.

* * * * *